United States Patent
Carmosin et al.

[11] Patent Number: 6,063,803
[45] Date of Patent: May 16, 2000

[54] OCTAHYDROPYRROLO-[3,4-C] CARBAZOLES USEFUL AS ANALGESIC AGENTS

[75] Inventors: Richard J. Carmosin, deceased, late of Quakertown, by Susan Carmosin, executrix; John R. Carson, Norristown; Philip M. Pitis, North Wales, all of Pa.

[73] Assignee: Ortho-McNeil Pharmaceutical, Inc., Raritan, N.J.

[21] Appl. No.: 09/305,215

[22] Filed: May 4, 1999

Related U.S. Application Data

[60] Provisional application No. 60/089,515, Jun. 16, 1998.

[51] Int. Cl.$^7$ .......................... A61K 31/40; C07D 209/80
[52] U.S. Cl. ............................................. 514/410; 548/420
[58] Field of Search ............................... 548/420; 514/410

[56] References Cited

U.S. PATENT DOCUMENTS 4,841,045  6/1989  Kuehne .................................... 540/478

*Primary Examiner*—Deborah C. Lambkin
*Attorney, Agent, or Firm*—John Harbour

[57] ABSTRACT

This invention relates to a series of compounds of Formula I

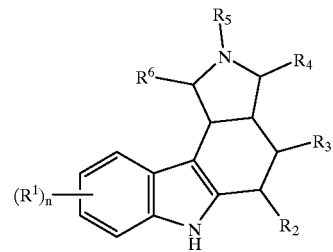

pharmaceutical compositions containing them and intermediates used in their manufacture. Compounds of the invention alleviate pain in animal models at levels comparable to known analgesic agents. As such the compounds are useful in the treatment of pain.

18 Claims, No Drawings

OCTAHYDROPYRROLO-[3,4-C] CARBAZOLES USEFUL AS ANALGESIC AGENTS

Provisional Application No. 60/089,515 Jun. 16, 1998.

FIELD OF THE INVENTION

This invention relates to a series of octahydropyrrolocarbazoles, pharmaceutical compositions containing them, intermediates used in their manufacture, as well as processes of their manufacture. The compounds of the invention bind to α-adrenergic receptors in human and animal models. In addition, the compounds demonstrate in vivo analgesic activity in animal models. As such the compounds are potentially useful in the treatment pain as well as diseases associated with α-adrenergic receptors.

BACKGROUND OF THE INVENTION

The treatment and management of pain has long been a goal of pharmacologists, physicians, and drug manufactures. Currently, pain is managed with opioids such as codeine and morphine, non-opioid agents such as aspirin, ibuprofen, and acetaminophen, as well as opioid/non-opioid agents such as tramadol. When treating their patients, physicians must balance the severity of the pain to be relieved with the efficacy of agent and its side effects. This balance is often difficult to achieve. Consequently, there is a pressing need for novel analgesics agents which will afford the physician improved opportunities to relieve pain.

SUMMARY OF THE INVENTION

The invention relates to compounds of the Formula I

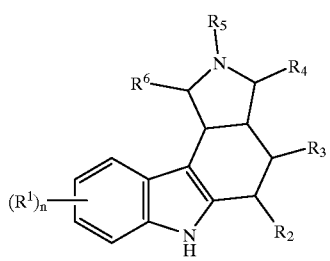

I wherein:
$R^1$ is independently selected from one or more members of the group consisting of halogen, hydrogen, $C_{1-5}$alkyl, trifluoromethyl, $C_{1-5}$alkoxy, $C_{1-5}$alkylthio, amido, cyano, alkenyl, alkynyl, $C_{1-5}$alkoxycarbonyl, $C_{1-5}$alkylcarbonyl, phenyl, phenylcarbonyl, $C_{1-5}$alkylsulfonyl, phenylsulfonyl,
substituted phenyl
where the phenyl substituents are selected from group consisting of $C_{1-5}$alkyl, $C_{1-5}$alkoxy, cyano, and halogen; and
substituted phenylcarbonyl
where the phenyl substituents are selected from group consisting of $C_{1-5}$alkyl, $C_{1-5}$alkoxy, cyano, and halogen; and
substituted phenylsulfonyl
where the phenyl substituents are selected group consisting of $C_{1-5}$alkyl, $C_{1-5}$alkoxy, cyano, halogen;

$R^2$ is hydrogen, $C_{1-5}$alkyl, phenyl, phenyl$C_{1-5}$alkyl, substituted phenyl
where the phenyl substituents are selected group consisting of $C_{1-5}$alkyl, $C_{1-5}$alkoxy, cyano, halogen; or
substituted phenyl$C_{1-5}$alkyl
where the phenyl substituents are selected group consisting of $C_{1-5}$alkyl, $C_{1-5}$alkoxy, cyano, and halogen;

$R^3$ is hydrogen, $C_{1-5}$alkyl, phenyl, phenyl$C_{1-5}$alkyl, substituted phenyl
where the phenyl substituents are selected group consisting of $C_{1-5}$alkyl, $C_{1-5}$alkoxy, cyano, halogen; or
substituted phenyl$C_{1-5}$alkyl
where the phenyl substituents are selected group consisting of $C_{1-5}$alkyl, $C_{1-5}$alkoxy, cyano, and halogen;

$R^4$ is hydrogen or $C_{1-5}$alkyl;
$R^5$ is hydrogen, $C_{1-5}$alkyl, $C_{1-5}$alkenyl, or $C_{1-5}$alkynyl
$R^6$ is hydrogen or $C_{1-5}$alkyl;
n is 1–4; and
pharmaceutically acceptable salts thereof.

DETAILED DESCRIPTION OF THE INVENTION

The terms used in describing the invention are commonly used and known to those skilled in the art. However, the terms that could have other meanings are defined. "Independently" means that when there are more than one substituent, the substitutents may be different. The term "alkyl" refers to straight, cyclic and branched-chain alkyl groups and "alkoxy" refers O-alkyl where alkyl is as defined supra. The symbol "Ph" refers to phenyl. The term "effective dose" refers to an amount of a compound of Formula I which alleviates pain in a patient. In addition, the term "effective dose" refers to an amount of a compound of Formula I which reduces the symptoms of diseases associated with the α-adrenergic receptor.

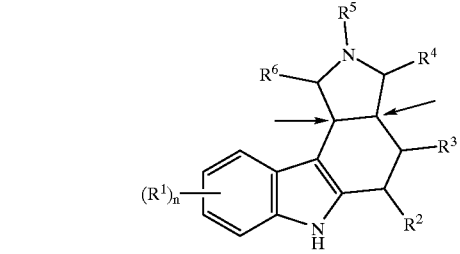

All of the compounds of the invention have at least two chiral centers. The invention contemplates compounds where the ring junctions (indicated by arrows) are either cis or trans, and the relative stereochemistry is determined by the method of synthesis. Schemes 1 and 2, prepare compounds with a cis ring junction, while Scheme 3 prepares the trans isomer. Most of the compounds of the invention are isolated as racemic mixtures of the cis or trans isomers. However, those racemic mixtures may be separated into pure enantiomers. Unless otherwise indicated, the illustrations within the schemes reflect the relative stereochemistry and should not be viewed as representing the absolute configuration of the compounds. There are another 4 possible stereocenters in compounds of Formula I. In addition to the aforementioned ring isomers, this invention contemplates all other possible stereoisomers.

The compounds of the invention may be prepared by the following schemes, where some schemes produce more than one embodiment of the invention. In those cases, the choice of scheme is a matter of discretion which is within the capabilities of chemists.

Compounds of Formula I where $R^1$ is halogen, hydrogen, $C_{1-5}$alkyl, trifluoromethyl, $C_{1-5}$alkoxy, $C_{1-5}$alkylthio, alkenyl, alkynyl, $C_{1-5}$alkylcarbonyl, phenyl, $C_{1-5}$alkylsulfonyl, phenylsulfonyl, substituted phenyl, and substituted phenylsulfonyl; n is 1–4; $R^5$ is alkyl or benzyl; $R^2$, $R^3$, $R^4$, and $R^6$ are hydrogen; and the ring juncture is cis, may be prepared as illustrated by Scheme 1. Triones of type 1a (prepared by the method of Reed et al. The Regioselectivity of the Formation of Dihydro- and Tetrahydrocarbazoles by the Fisher Indole Synthesis, *Can. J. Chem.* 1982, 60, 419–24), are heated with an $R^1$ substituted phenyl hydrazine derivatives of type 1b, and a mild base such as sodium acetate in an inert solvent such as ethanol at reflux for 1–6 h. The crude products are treated with an acidic solution, such as concentrated $H_2SO_4$, a solvent such as methanol, and heated at reflux for about 0.5 to 100 h to give the diones, 1c. Alternatively, the diones 1c may be produced in a similar reaction, where conc $H_2SO_4$ is replaced by phosphorous trichloride $ZnCl_2$, TFA or acetic acid. These diones may be treated with a reducing agent such as aluminum hydride or borane, in an inert solvent such as THF at 0° C. over 1–24 h to give a compounds of type 1d, as a racemic mixture. These mixtures may be separated into pure enantiomers by high pressure liquid chromatography using chiral columns and suitable solvents or classical resolution techniques.

Compounds where $R^5$ is hydrogen, alkenyl or alkynyl may be prepared by synthesizing a compound of Formula I where $R^5$ is benzyl and removing the benzyl group via hydrogenation with Pd/C to give the corresponding product where $R^5$ is hydrogen. This product may be treated with a base, such as $K_2CO_3$, or $NaHCO_3$, and an alkylating agent such as allyl bromide or propargyl bromide to give a compound where $R^5$ is alkenyl or alkynyl, respectively.

Scheme 1

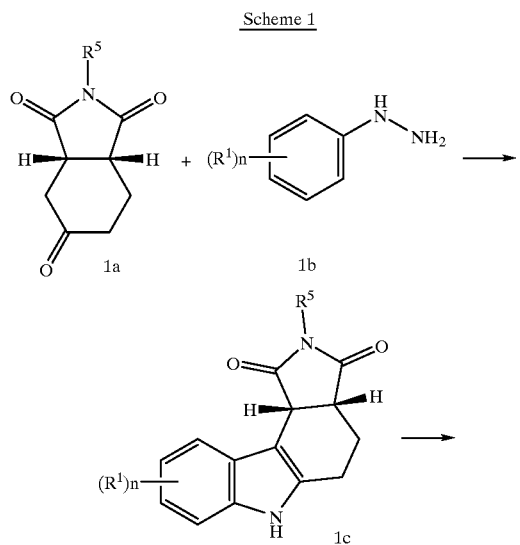

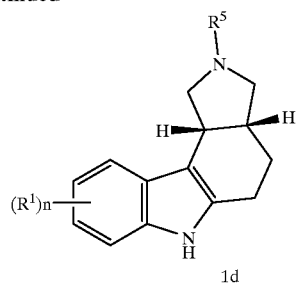

1d $R^1$'s, such as cyano, $C_{1-5}$alkoxycarbonyl, amido are susceptible to reduction with aluminum hydride. Therefore in order to prepare these compounds some additional steps must be added to Scheme 1as illustrated Scheme 1a. This scheme converts a compound of Formula I where $R^1$ is halogen, such as 1g, to a nitrile 1h using copper (I) cyanide and DMF in the presence of a palladium catalyst such as tetrakis(triphenylphosphine)palladium 0 at about 120° C. over 1–6 days. This nitrile may be subsequently hydrolyzed in the presence of an aqueous acid, such as $H_2SO_4$, or a base such as NaOH, and esterified using an alcohol such as ethanol to give compounds of Formula I where $R^1$ is $C_{1-5}$alkoxycarbonyl. Compounds where $R^1$ is amido may also be prepared by this method from the corresponding carboxylic acid derivatives.

Scheme 1a

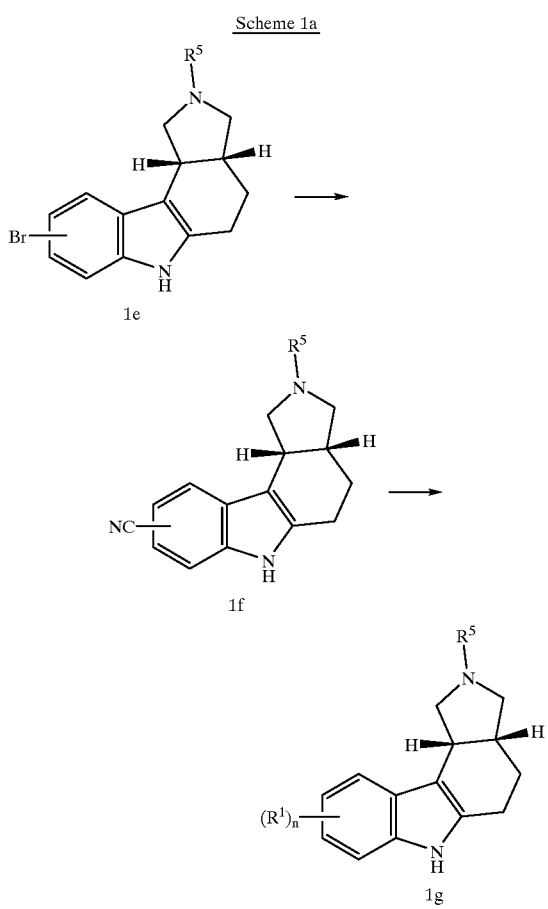

To prepare compounds where $R^1$ is $C_{1-5}$alkylcarbonyl, phenylcarbonyl, substituted phenylcarbonyl, the starting material of Scheme 1a may be used. Treatment of 1e with n-BuLi in an inert solvent such as THF at −78 to 0° C. gives the corresponding lithium derivative. Treatment of this intermediate with an acylating agent, such N-methoxy-N-methylbenzamide, at 0° C. gives a compound of Formula I where $R^1$ is phenylcarbonyl. This method can be used to prepare $C_{1-5}$alkylcarbonyl and substituted phenylcarbonyl compounds by replacing N-methoxy-N-methylbenzamide with an acylating agent such as N-methoxy-N-methylacetamide or 4'-chloro-N-methylbenzamide.

To prepare compounds where $R^6$ is $C_{1-5}$alkyl, Scheme 1b may be used. Treatment of intermediates of type 1c with DIBAL in THF at about −78° C. gives the hydroxy compounds, 1h. These compounds may be treated with triethylsilane and trifluoroacetic acid in nitromethane to give the 1-one derivatives 1i. Treatment of these derivatives with an alkyllithium reagents followed by LAH/THF gives the desired compounds of type 1j where the ring juncture is cis.

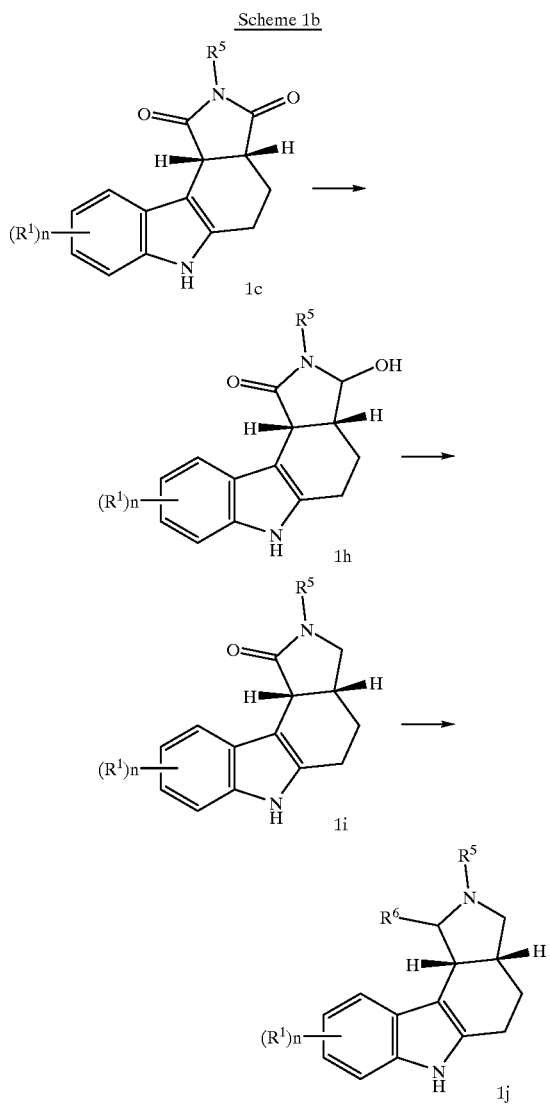

Scheme 1b

To prepare compounds where $R^4$ is $C_{1-5}$alkyl, intermediate 1c may be used as illustrated by Scheme 1c. Treatment of intermediate 1c with $NaBH_4$ in THF at about −78° C. gives compounds of type 1k. These compound may be treated with triethylsilane and trifluoroacetic acid in nitromethane to give compounds of type 1l. Treatment of these intermediate with an alkyllithium reagents and LAH/THF give compounds of type 1m.

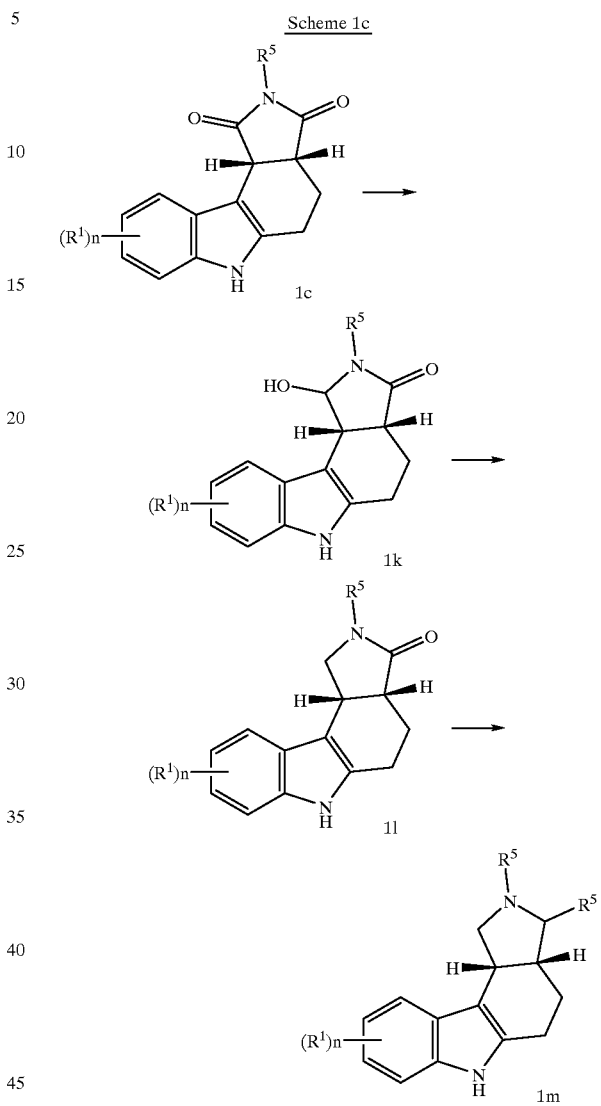

Scheme 1c

Another method of preparing the cis fused compounds is illustrated by Scheme 2. This scheme may be used to produce compounds where $R^2$ and $R^3$ are hydrogen, $C_{1-5}$alkyl, phenyl or phenyl$C_{1-5}$alkyl. Maleimide derivatives of type 2a, are treated with 2-substituted vinyl indole derivatives (substituted vinyl indoles may be prepared by a number of known methods M. Eitel & U. Pindur, "Selective Wittig Reaction for the Synthesis of Variously Substituted 2-Vinylindoles," *Synthesis*, 1989, 364–67; U. Pindur & M. Eitel, "First Synthesis of 2-Vinylindole and its Diels-Alder Reactions with CC-Dienophiles," *Helvetica Chemica Acta* 1988, 71, 1060–63), 2b in a suitable solvent such as toluene at reflux for 5–20 h to give compounds of type 2c. These compounds may be reduced with aluminum hydride in an inert solvent such at THF at 0° C. over 1–7 h to give the compounds of type 2d.

To produce all of the other $R^1$, $R^5$, $R^4$ and $R^6$ substitutents, the modifications that were illustrated for Scheme 1 may be used for Scheme 2.

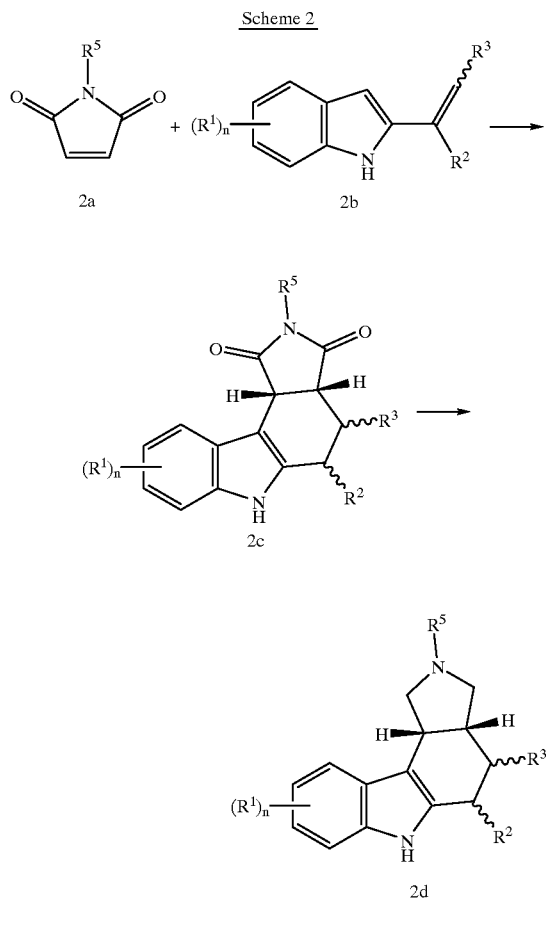

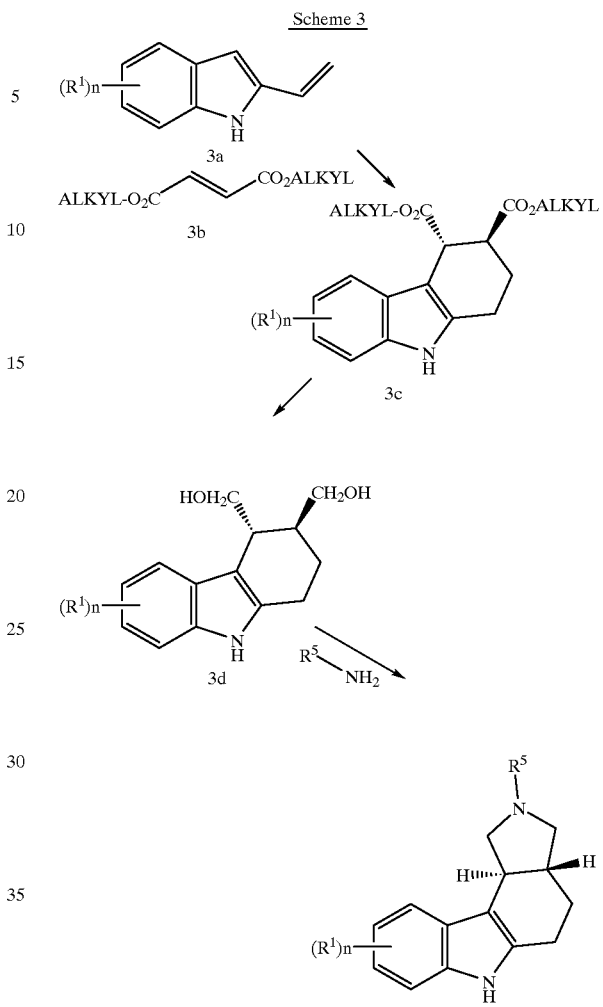

Scheme 3 may be used to produce the trans ring juncture. Appropriately substituted 2-vinyl indoles of type 3a are heated with dialkyl fumarate esters, 3b, in xylene in a closed system at about 100° C. over 10–24 h to give the diesters, 3c. Treatment of diesters of type 3c with reducing agents, such as LAH, give dihydroxy compounds, 3d. The hydroxyl groups may be converted to corresponding mesylates using mesyl chloride at 0° C. and subsequently treated with a substituted amine derivative 3d in an inert solvent at 80–100° C. to give the desired trans product as racemic mixtures.

Using methods analogous to Schemes 1 and 2, many compounds of Formula I may be prepared using this scheme. For example, to produce compounds with varying $R^1$ groups, replace the illustrated 3a with any of a number of vinyl indoles. If the desired $R^1$ substituent is susceptible to reduction with hydride reducing agents, the methods employed in Scheme 1a and Scheme 1b may be used. To produce a variety of $R^5$ groups, the illustrated amine derivative, 3d may be replaced with a number of alkylamines, such t-butylamine. To produce a variety of $R^3$ and $R^2$ groups, starting materials of type 3a may be replaced with 2 or 3 substituted vinyl indoles in the manner of Scheme 2.

When compounds contain a basic moiety, acid addition salts may be prepared and may be chosen from hydrochloric, hydrobromic, hydroiodic, perchloric, sulfuric, nitric, phosphoric, acetic, propionic, glycolic, lactic, pyruvic, oxalic, malonic, succinic, maleic, fumaric, malic, tartaric, citric, benzoic, cinnamic, mandelic, methanesulfonic, p-toluenesulfonic, cyclohexanesulfamic, salicylic, 2-phenoxybenzoic, 2-acetoxybenzoic, or saccharin, and the like. Such salts are made by reacting the free base of compounds of Formula I with the acid and isolating the salt.

Although the claimed compounds are effective analgesic agents, some are more active than other and are either preferred or particularly preferred. The preferred compounds of the invention include:

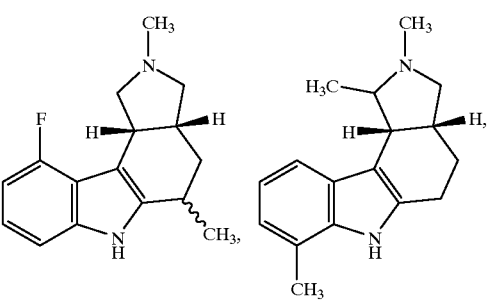

-continued

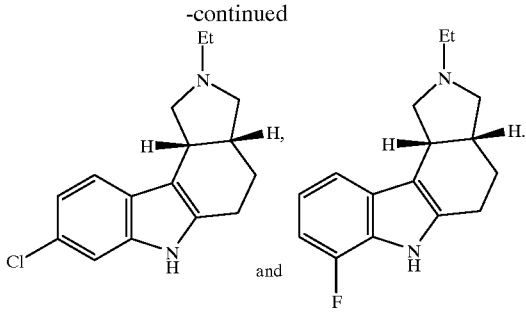

The particularly preferred compounds of the invention include compounds where the ring junction is cis and $R^1$ is hydrogen, halogen, $C_{1-5}$alkyl, trifluoromethyl, or nitrile;

$R^2$ is hydrogen;

$R^3$ is hydrogen;

$R^4$ is hydrogen;

$R^5$ is $C_{1-5}$alkyl;

$R^6$ is hydrogen;

The compounds of this invention are novel compounds which demonstrate in vivo analgesic activity in animal models, at a potency which is comparable to or greater than known analgesic agents. In particular the compounds were compared to the analgesic agent tramadol. Tramadol is currently being marketed under the tradename Ultram® and is used in the management of pain severe to moderate pain associated with a variety of surgical procedures. Select compounds of the invention have comparable activity to tramadol in rodent abdominal constriction assays and superior activity in rodent hot plate assays. These assays are of a class of test which are highly predictive of analgesic effects in humans. (H. Collier, et al., Abdominal Constriction Response and its Suppression by Analgesic Drugs in the Mouse, Br. *J. Pharmacol. Chemother.*, 32(2), 295 (1968)). As such the compounds of the invention are potentially useful in the treatment of pain in man.

In addition to in vivo analgesic activity, compounds of the invention inhibit the binding of natural ligands to the $\alpha_1$ and $\alpha_2$-adrenergic receptors in the nanomolar range. As such compounds of Formula I may be useful for the treatment disorders associated with those receptors including but not limited to hypertension or sleep disorders.

To prepare the pharmaceutical compositions of this invention, one or more compounds or salts thereof, as the active ingredient, is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will preferably contain per dosage unit, e.g., tablet, capsule, powder, injection, teaspoonful and the like, from about 5 to about 500 mg of the active ingredient, although other unit dosages may be employed.

To alleviate pain in a mammal, the compounds of this invention may be administered in an amount of from about 5–1000 mg/kg 1–2 times per day orally. Some compounds may be administered in an amount of 25–100 mg/kg 1–2 times per day orally. In addition the compounds may be administered via injection at 1–200 mg/kg per day or 5–25 mg/kg per day. For topical administration compounds of Formula I may be mixed with a pharmaceutical carrier at a concentration of about 1.0 to about 10% of drug to vehicle. Determination of optimum dosages for a particular situation is within the capabilities of formulators.

In order to illustrate the invention, the following examples are included. These examples do not limit the invention. They are meant to illustrate and suggest a method of practicing the invention. Although there are other methods of practicing this invention, those methods are deemed to be within the scope of this invention.

Example 1

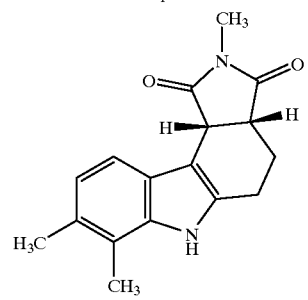

(±)-3aα,10cα-4,5,6,10c-Tetrahydro-2,7,8-trimethylpyrrolo[3,4-c]carbazole-1,3-(2H,3aH)-dione Cpd. 1

A mixture of 5.1 g (28 mmol) of 2-methyltetrahydro-1H-isoindole-1,3,5-(2H,4H)-trione, 4.84 g (28 mmol) of 2,3-dimethylphenylhydrazine hydrochloride and 4.62 g (56 mmol) of sodium acetate was heated under reflux for 2.5 h. The mixture was poured into water and the solid was collected and air dried. The crude hydrazone, thus obtained, was added to a solution of 7 mL of conc. $H_2SO_4$ in 38 mL of MeOH. The mixture was heated under reflux for 0.5 h. The solution was poured into $K_2CO_3$ solution and extracted with $CH_2Cl_2$. The solution was dried ($Na_2SO_4$) and the solvent evaporated. The residue was recrystallized from 2-PrOH and twice from EtOAc to afford 1.5 g (19%) of (±)-3aα,10cα-4,5,6,10c-tetrahydro-2,7,8-trimethylpyrrolo[3,4-c]carbazole-1,3-(2H,3aH)-dione: mp 239–244° C. Cl-MS m/z=283 (M+H). $^1$H NMR (CDCl$_3$) δ 7.7 (s, 1H); 7.6 (d, 1H); 7.0 (d, 1H); 4.38 (m, 1H); 3.37 (m, 1H); 2.9 (s, 3H); 2.7 (m, 3H); 2.37 (s, 3H); 2.3 (s, 3H); 1.95 (m, 1H). Anal calcd. for $C_{17}H_{18}N_2O_2$: C, 72.32; H, 6.43; N, 9.92. Found: C, 72.06; H, 6.45; N, 9.77.

Example 2–18

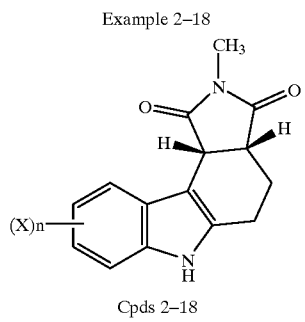

Cpds 2–18

Following the experimental description of Example 1 and substituting the appropriately substituted phenylhydrazine for 2,3-dimethylphenylhydrazine, the following (±)-3aα,10cα,4,5,6,10c-tetrahydro-2-methylpyrrolo[3,4-c]carbazole-1,3-(2H,3aH)-diones were obtained:

| Cpd. | Reaction Time (hr) | X | purification[a] | MS m/z (m+) | mp ° C. |
|---|---|---|---|---|---|
| 2 | 6 | 9-F | B | 273 | 199–200 |
| 3 | 24 | 7,10-diCl | A | 323 | 273–274 |
| 4 | 2 | 7-Cl | A | 289 | 215–216 |
| 5 | 3 | 9-Br | A | 333 | 243–245 |
| 6 | 8 | 8-Cl | D | 289 | 219–220 |
| 7 | 8 | 10-Cl | D | 289 | 250–252 |
| 8 | 3 | 9-iPr | C | 297 | 171–173 |
| 9 | 16 | 8-CF$_3$ | D | 323 | 239–240 |
| 10 | 16 | 10-CF$_3$ | D | 323 | 241–242 |
| 11 | 5 | 7-Br | A | 333 | |
| 12 | 3 | 7-Et | B | 307 | |
| 13 | 4 | 7-F | B | 290 | |
| 14 | 24 | 7-CF$_3$ | B | 323 | 136–139 |
| 15 | 3 | 8,10-diCH$_3$ | B | 283 | 257–260 |
| 16 | 72 | 8,10-diF | B | 291 | 247–249 |
| 17 | 7.5 | 8-Br | B | 334 | OIL |
| 18[b] | 6 | 9-CH$_3$O | C | 285 | 210–211 |

[a]Purification methods: A. crystallization from EtOAc. B. Flash chromatography on silica gel: CH$_2$Cl$_2$: hexane: EtOAc (3:3:2). C. Flash chromatograpy on silica gel: EtOAc: hexane (1:1). D. Flash chromatograpy on silica gel: EtOAc: toluene (3:7).
[b]4% (wt/vol) H$_2$SO$_4$ in MeOH used as reaction medium.

Example 19

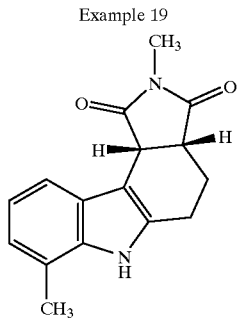

(±)-3aα,10cα-4,5,6,10c-Tetrahydro-2,7-dimethylpyrrolo[3,4-c]carbazole-1,3-(2H,3aH)-dione

Cpd. 19

A solution of 12.1 g (0.067 mol) of tetrahydro-2-methyl-1 H-isoindole-1,3,5-(2H,4H)-trione, 10.6 g (0.067 mol) o-tolylhydrazine hydrochloride, 10.9 g (0.134 mol) of NaOAc and 200 mL of EtOH was refluxed for 2.5 h. The reaction mixture was poured into water and the solid was filtered off. After air drying, 12.77 g (0.044 mol) of the hydrazone was dissolved in 250 mL of CH$_2$Cl$_2$ and 10.2 mL (0.11 mol) PCl$_3$ added. The reaction was stirred for 5 h then poured into water. The organics were washed with water, brine, and dried (Na$_2$SO$_4$). The solvent was evaporated in vacuo and the residue recrystallized from EtOAc. The mother liquors were flash chromatographed on silica gel: CH$_2$Cl$_2$:hexane:EtOAc (3:3:2) and then recrystallized from EtOAc. The batches were combined to give 5.53 g (46%) of a solid: mp 211–215° C. Cl-MS m/z=269 (M+H). $^1$H NMR (CDCl$_3$) δ 7.8 (d, 2H); 7.1 (q, 1H); 7.0 (Ar, H); 4.3 (d, 1H); 3.35 (m, 1H); 2.9 (s, 3H); 2.8–2.55 (m, 3H); 2.45 (s, 3H); 2.0 (m, 1H).

Example 20

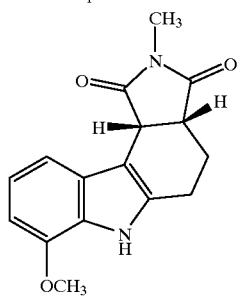

(±)-3aα,10cα-4,5,6,10c-Tetrahydro-7-methoxy-2-methylpyrrolo[3,4-c]carbazole-1,3-(2H,3aH)-dione

Cpd. 20

A solution of 4.8 g (0.028 mol) of tetrahydro-2-methyl-1H-isoindole-1,3,5-(2H,4H)-trione, 5.0 g (0.028 mol) of o-methoxyphenylhydrazine hydrochloride, 4.7 g (0.059 mol) of NaOAc and 100 mL of EtOH was refluxed for 4.5 h. The reaction mixture was poured into water. The solution was extracted with CHCl$_3$, the organics were washed with water, brine and dried (Na$_2$SO$_4$). The solvent was evaporated in vacuo. The residue was taken up in 200 mL of HOAc and refluxed for 4.5 h. The HOAc was concentrated in vacuo then poured into aqueous NaHCO$_3$. The solution was extracted with Et$_2$O and the organics were washed with water, brine and dried (K$_2$CO$_3$). The solvent was evaporated in vacuo. The residue was flash chromatographed twice on silica gel (1:1 EtOAc:hexane then 2:2:1 CH$_2$Cl$_2$:hexane:EtOAc) to give 3.01 g of (±)-3aα,10cα-4,5,6,10c-tetrahydro-7-methoxy-2-methylpyrrolo[3,4-c]carbazole-1,3-(2H, 3aH)-dione: mp 237–238° C. Cl-MS m/z=285 (M+1). $^1$H NMR (CDCl$_3$) δ 8.1 (br s, 1H); 7.6 (d, 1H); 7.1 (t, 1H); 6.65 (d, 1H); 4.3 (d, 1H); 3.95 (s, 3H); 3.4 (m, 1H); 2.9 (s, 3H); 2.8–2.55 (m, 3H); 2.0 (m, 1H).

Example 21

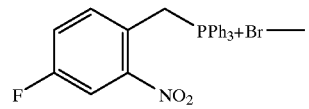

[(4-Fluoro-2-nitrophenyl)methyl] triphenylphosphonium Bromide

Cpd. 21

A solution of 117 g (0.5 mol) of 2-nitro-4-fluorobenzyl bromide and 131 g (0.5 mmol) of triphenylphosphine in 2 L of EtOAc was heated under reflux for 3 h. The mixture was cooled and the solid collected to give 175 g (70%) of [(4-fluoro-2-nitrophenyl)methyl]triphenylphosphonium bromide: $^1$H NMR (CDCl$_3$) δ 8.2 (m, 1H); 7.8–7.5 (m, 16H); 7.4 (m, 1H); 6.1 (d, 2H).

Example 22

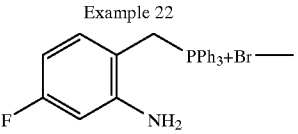

[(2-Amino-4-fluorophenyl)methyl]
triphenylphosphonium Bromide

Cpd. 22

A solution of 175 g (0.35 mol) of [(4-fluoro-2-nitrophenyl)methyl]-triphenylphosphonium bromide in 760 mL of EtOH and 380 mL of 48% HBr was brought to reflux and 138 g (2.1 mol) of zinc dust was added in portions over 4 h and refluxed further for 2 h. The mixture was cooled and the EtOH evaporated. The residue was partitioned between CH$_2$Cl$_2$ and H$_2$O. The CH$_2$Cl$_2$ solution was washed with 7M NH$_4$OH. The aqueous phase was decanted and the precipitate dissolved in CH$_2$Cl$_2$/EtOH. The organic phase was washed with brine, dried (Na$_2$SO$_4$) and concentrated. There was obtained 89 g (54%) of [(2-amino-4-fluorophenyl)methyl]triphenylphosphonium bromide as a solid: $^1$H NMR (Me$_2$SO-d$_6$) δ 8.0–7.6 (m, 15H); 6.6 (m, 1H); 6.4 (m, 1H); 6.15 (m, 1H); 5.5 (br s, 2H); 4.95 (d, 2H).

Example 23

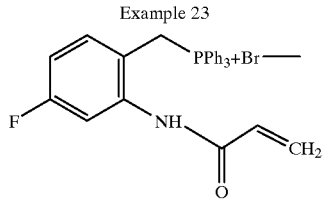

[[4-Fluoro-2-[(1-oxo-2-propenyl)amino]phenyl]
methyl]triphenylphosphonium Bromide Cpd. 23

A suspension of 89 g (0.19 mol) of [(2-amino-4-fluorophenyl)methyl]-triphenylphosphonium bromide in 1.5 L CH$_2$Cl$_2$ was stirred and 17 mL (0.21 mol) of acryloyl chloride was added dropwise. A 22.8 mL sample of pyridine was added dropwise. The mixture was heated under reflux for 45 min. The mixture was cooled, washed with K$_2$CO$_3$ solution, dilute hydrochloric acid and brine. It was dried (Na$_2$SO$_4$), concentrated and triturated with Et$_2$O to give 80 g (81%) of [[4-fluoro-2-[(1-oxo-2-propenyl)amino]phenyl] methyl]triphenylphosphonium bromide as a yellowish solid: $^1$H NMR (CDCl$_3$) δ 8.0–7.4 (m, 15H); 6.9 (m, 2H); 6.4 (m, 1H); 6.1 (d, 1H); 5.9 (d, 2H); 5.5 (d, 1H).

Example 24

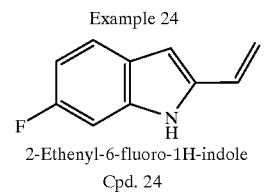

2-Ethenyl-6-fluoro-1H-indole

Cpd. 24

A 71.5 g (0.14 mol) sample of [[4-fluoro-2[(1-oxo-2-propenyl)amino]phenyl]-methyl]triphenylphosphonium bromide was suspended in 1.6 L of toluene and heated under reflux briefly with azeotropic removal of water. A 180 mL (0.18 mol) solution of 1M potassium t-butoxide in THF was added dropwise under Ar. The mixture was heated under reflux for one hour, cooled, washed with dilute HCl and filtered. The organic phase was washed with brine, dried (MgSO$_4$) and concentrated. The residue was crystallized from methyl t-butyl ether (MTBE)/hexane. The precipitated triphenylphosphine oxide was collected and washed with MTBE. The combined filtrates were concentrated and flash chromatographed twice using EtOAc:hexane 1:10 as eluant. There was obtained 11.3 g (50%) of 2-ethenyl-6-fluoro-1H-indole: Cl-MS m/z=162 (M+H). $^1$H NMR (CDCl$_3$) δ 8.1 (br s, 1H); 7.5 (m, 1H); 7.0 (d, 1H); 6.85 (m, 1H); 6.7 (m, 1H); 6.5 (s, 1H); 5.5 (d, 1H); 5.25 (d, 1H).

Example 25

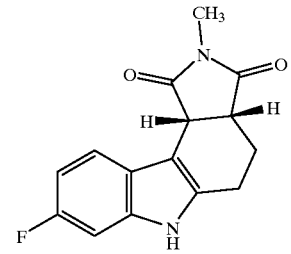

(±)-3aα,10cα-4,5,6,10c-Tetrahydro-8-fluoro-2-methylpyrrolo[3,4-c]carbazole-1,3-(2H,3aH)-dione Cpd. 25

A solution of 11.3 g of 2-ethenyl-6-fluoroindole and 7.8 g (0.07 mol) of N-methylmaleimide in 500 mL of toluene was heated under reflux for 16 h. The solvent was evaporated and the residue crystallized from CH$_3$CN to give 6.4 g of solid. The mother liquors were evaporated and the residue was flash chromatographed on SiO$_2$ using EtOAc:CH$_2$Cl$_2$:hexane, 1:2:2 as eluant. In total, 10.2 g (53%) of (±)3aα,10cα-4,5,6,10 c-tetrahydro-8-fluoro-2-methyl-pyrrolo[3,4-c]carbazole-1,3-(2H, 3aH)-dione were obtained: mp 238–239° C. Cl-MS m/z=273 (M+H). $^1$H NMR (CDCl$_3$) δ 7.9 (m, 2H); 6.95 (m, 2H); 4.3 (d, 1H); 3.35 (m, 1H); 2.95 (s, 3H); 2.7 (m, 3H); 2.7 (m, 3H); 2.0 (m, 1H). Anal calcd. for C$_{15}$H$_{13}$FN$_2$O$_2$: C, 65.09; H, 4.92; N, 10.12. Found: C, 65.11; H, 4.83; N, 10.05.

Example 26

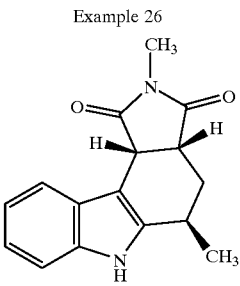

(±)-3aα,5α,10cα-4,5,6,10c-Tetrahydro-2,5-dimethylpyrrolo[3,4-c]carbazole-1,3-(2H,3aH)-dione Cpd. 26

A solution of 8.2 g (0.051 mol) 2-(1-methylethenyl)-1H-indole, 200 mL of toluene and 7.9 g (0.066 mol) N-methylmaleimide was refluxed for 10 h then stirred at room temperature for 72 h. The reaction was poured into water and extracted with $CH_2Cl_2$. The organics were washed with water, brine and dried ($Na_2SO_4$). The residue was crystallized from EtOAc which yielded 4.76 g (35%) of a solid, single diastereomer: mp 238–239° C. Cl-MS m/z=269 (M+H). $^1$H NMR ($CDCl_3$) δ 8.0 (m, 1H); 7.4–7.1 (m, 3H); 4.35 (d, 1H); 3.4 (m, 1H); 2.95 (m, H); 3.0 (s, 3H); 2.75–2.4 (m, 1H); 1.7–1.5 (m, 1H); 1.4 (d, 3H).

Example 27

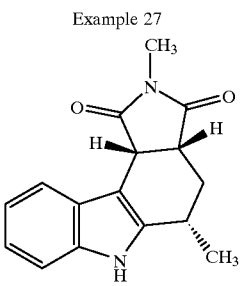

(±)-3aα,5β,10cα-4,5,6,10c-Tetrahydro-2,5-dimethylpyrrolo[3,4-c]carbazole-1,3-(2H,3aH)-dione Cpd. 27

The filtrate from the above recrystallization was evaporated in vacuo and chromatographed on silica gel [(50:50, $CH_2Cl_2$:hexane) 3:1 EtOAc] to give 1.03 g (7.6%) of a peach solid. mp 244–246° C. Cl-MS m/z=269 (M+H). $^1$H NMR ($CDCl_3$) d 8.0 (m,1H); 7.4–7.1 (m, H); 4.25 (d, 1H); 3.3 (q, 1H); 3.1 (q, 1H); 3.0 (s, 3H); 2.4–2.3 (m, 1H); 2.0–1.9 (m, 1H); 1.3 (d, 3H). Anal calcd for $C_{16}H_{16}N_2O_2$: C, 71.62; H, 6.80; N, 10.44. Found: C, 71.30; H, 6.41; N, 10.34.

Example 28

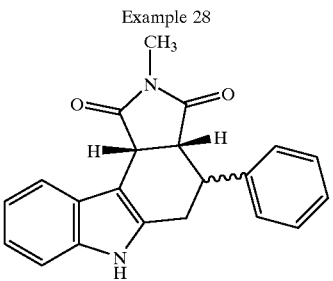

(±)-3aα,10cα-4,5,6,10c-Tetrahydro-2-methyl-4-phenylpyrrolo[3,4-c]carbazole-1,3-(2H,3aH)-dione Cpd. 28

A solution of 3.53 g (0.016 mol) of 2-(2-phenylethenyl)-1H-indole, 1.8 g (0.016 mol) of N-methylmaleimide and 70 mL of xylene was placed into a pressure bottle and heated to 120° C. overnight. The reaction was poured into water. The organics were washed with water, brine and dried ($Na_2SO_4$). The solvent was evaporated in vacuo. Flash chromatography on silica gel (3:1 hexane:acetone) gave 1.4 g of the product and 3.5 g of 2-(2-phenylethenyl)-1H-indole. The recovered starting material was placed in a pressure bottle with 1.5 g (0.0135 mole) of N-methylmaleimide and 70 mL of xylene and heated to 120° C. overnight. The reaction was worked-up as above to give 3.1 g of a dark oil (58%). Cl-MS m/z=330 (M+H). $^1$H NMR ($CDCl_3$) δ 8.2 (br s, 1H); 8.0 (s, 1H); 7.4–7.0 (m, H); 4.4 (d, 1H); 3.65 (m, 1H); 3.5 (m, 1H); 3.25–3.1 (m, H); 3.05–2.9 (m, 1H); 2.7 (s, 3H).

Example 29

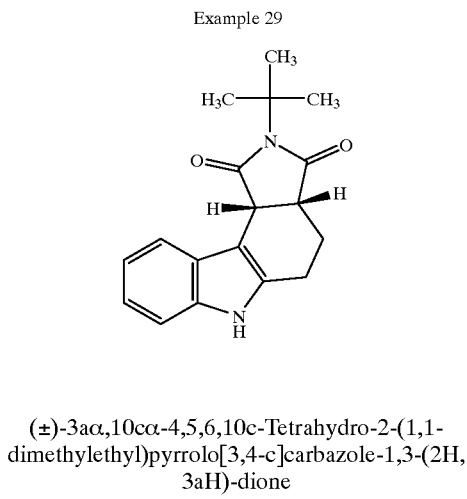

(±)-3aα,10cα-4,5,6,10c-Tetrahydro-2-(1,1-dimethylethyl)pyrrolo[3,4-c]carbazole-1,3-(2H,3aH)-dione Cpd. 29

A solution of 2.0 g (0.014 mol) of 2-ethenyl-1H-indole, 100 mL of toluene and 2.1 g (0.014 mol) of t-butylmaleimide was refluxed overnight. The solvent was evaporated in vacuo and the oil crystallized from toluene to give 2.73 g (66%) of solid: mp 179–181° C. Cl-MS m/z= 297. $^1$H NMR ($CDCl_3$) δ 7.9 (m, 1H); 7.35–7.1 (m, 3H); 4.15 (d, 1H); 3.2 (m, 1H); 2.7 (m, 2H); 2.4 (m, 1H); 1.9 (m, 1H); 1.5 (s, 9H). Anal calcd for $C_{18}H_{20}N_2O_2$: C, 72.94; H, 6.80; N, 9.45. Found: C, 73.15; H, 6.91; N, 9.61.

Example 30

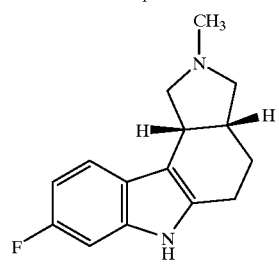

(±)-3aα,10cα-4,5,6,10c-Octahydro-8-fluoro-2-methylpyrrolo[3,4-c]carbazole Fumarate [1:1.5]

Cpd. 30

A 6 mL (0.112 mol) sample of conc. $H_2SO_4$ was added slowly to 337 mL (0.225 mol) of 0.67 M LAH in THF at 0° C. under Ar. The solution was stirred for 30 min at 0° C. A 10.2 g (0.038 mol) sample of (±)-3aα,10cα- 4,5,6,10c-tetrahydro-8-fluoro-2-methylpyrrolo[3,4-c]carbazole-1,3-(2H,3aH)-dione (cpd. 25) was added as a solid. The mixture was stirred at 0° C. for 3 h. A solution of 28.2 mL of 50% THF-water was added dropwise with cooling. The solid was filtered and washed with THF. The filtrate was concentrated and a fumarate salt was prepared from 2-PrOH. There was obtained 12.3 g (77%) of (±)-3aα,10cα-1,2,3,3a,4,5,6,10c-octahydro-8-fluoro-2-methylpyrrolo[3,4-c]carbazole fumarate [1:1.5] as a white solid: mp 182–184° C. Cl-MS m/z=245 (M+H). $^1$H NMR ($Me_2SO$-$d_6$) δ 7.4 (m, 1H); 7.15 (m, 1H); 6.8 (t, 1H); 6.5 (s, 3H); 3.6 (t, 1H); 3.5 (q, 1H); 3.35 (t, 1H); 2.7 (m, 5H); 2.6 (s, 3H); 1.85 (m, 2H). Anal calcd. for $C_{15}H_{17}FN_2$•1.5 $C_4H_4O_4$: C, 60.28; H, 5.54; N, 6.70. Found: C, 60.36; H, 5.50; N, 6.68.

Examples 31–53

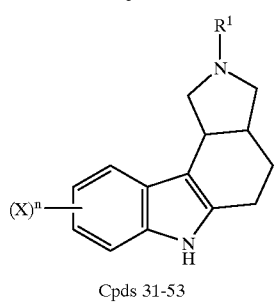

Cpds 31-53

Following the procedure of example 30 and employing the appropriately substituted (±)-3aα,10cα-4,5,6,10c-tetrahydro[3,4-c]carbazole-1,3-(2H,3aH)-dione in place of (±)-3aα,10cα-4,5,6,10c-tetrahydro-8-fluoropyrrolo[3,4-c]carbazole-1,3-(2H,3aH)-dione (cpd. 25), the following (±)-3aα, 10cα-1,2,3,3a,4,5,6,10c-octahydropyrrolo[3,4-c]carbazoles were obtained:

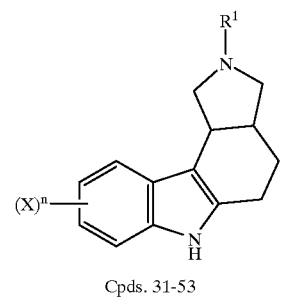

Cpds. 31-53

| # | $X^n$ | $R^1$ | salt (ratio) | MS (M$^+$) | mp ° C. |
|---|---|---|---|---|---|
| 31 | 9-F | 2-$CH_3$ | fumarate(1:1) | 245 | 169–170 |
| 32 | 7-$OCH_3$ | 2-$CH_3$ | fumarate(1:1.5) | 257 | 233–235 |
| 33 | 7,10-diCl | 2-$CH_3$ | free base | 295 | 203–205 |
| 34 | 7,8-di$CH_3$ | 2-$CH_3$ | fumarate(1:0.6) | 255 | 253–255 |
| 35 | 7-Cl | 2-$CH_3$ | free base | 261 | 169–171 |
| 36 | 9-Br | 2-$CH_3$ | fumarate(1:1.4) | 305 | 218–219 |
| 37 | 8-Cl | 2-$CH_3$ | hydrochloride | 261 | 250–251 |
| 38 | 10-Cl | 2-$CH_3$ | hydrochloride | 261 | 235–236 |
| 39 | 9-(2-Pr) | 2-$CH_3$ | free base | 269 | 152–154 |
| 40 | 7-$CH_3$ | 2-$CH_3$ | hydrochloride | 241 | 262–264 |
| 41 | 8-$CF_3$ | 2-$CH_3$ | hydrochloride | 295 | 215–216 |
| 42 | 10-$CF_3$ | 2-$CH_3$ | free base | 295 | 182–184 |
| 43 | 8-F | 2-$CH_3$ | fumarate(1:1.5) | 245 | 182–184 |
| 44 | 10-F | 2-$CH_3$ | hydrochloride | 245 | 271–273 |
| 45 | 7-Br | 2-$CH_3$ | fumarate(1:1) | 306 | 86–89 |
| 46 | 7-Et | 2-$CH_3$ | fumarate(1:1.4) | 255 | 186–188 |
| 47 | 7-F | 2-$CH_3$ | fumarate(1:0.5) | 245 | 179–181 |
| 48 | 7-$CF_3$ | 2-$CH_3$ | fumarate(1:1) | 295 | 181–183 |
| 49 | 8,10-di$CH_3$ | 2-$CH_3$ | fumarate(1:1) | 255 | 176–180 |
| 50 | 8,10-diF | 2-$CH_3$ | fumarate(1:1) | 263 | 203–204 |
| 51 | 9-$OCH_3$ | 2-$CH_3$ | fumarate(1:1.5) | 257 | 203–204 |
| 52 | 8-Br | 2-$CH_3$ | fumarate(1:1) | 306 | 169–170 |
| 53 | | 2-t-Bu | hydrochloride | 269 | 256–259 |

Example 54

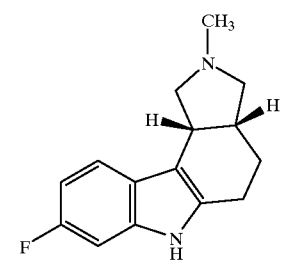

(±)-3aα,10cα-4,5,6,10c-Octahydro-8-fluoro-2-methylpyrrolo[3,4-c]carbazole Fumarate [1:1.5]

Cpd. 54

A 3.4 g sample of (±)-1,2,3,3aα,4,5,6,10cα-octahydro-8-fluoro-2-methylpyrrolo[3,4-c]carbazole (cpd. 30) was passed through a Chiralcel® OJ column with hexane: EtOH:MeOH:DEA 92%:4%:4%:0.01%. The first peak off the column was collected and converted to the fumarate salt in 2-PrOH to give 1.03 g of solid: mp 186–188° C. Cl-MS m/z=245 (M+H). $^1$H NMR δ 7.35 (m, 1H); 7.1 (dd, 1H); 6.8 (m, 1H); 6.5 (s, 2H); 3.7 (m, 1H); 3.6 (m, 1H); 2.9–2.6 (m, 5H); 2.6 (s, 3H); 1.8 (m, 2H). $[α]^D$=+93.21°. Anal calcd for $C_{15}H_{17}FN_2$•1.5 $C_4H_4O_4$: C, 60.28; H, 5.54; N, 6.70. Found: C, 60.32; H, 5.69; N, 6.65.

Example 55

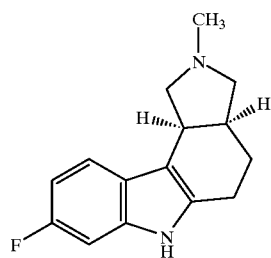

(−)-3aα,10cα-4,5,6,10c-Octahydro-fluoro-2-methylpyrrolo[3,4-c]carbazole Fumarate [1:1.5]

Cpd. 55

The second peak from the foregoing example was converted to the fumarate salt in 2-PrOH to give 1.23 g of solid: mp 185–188° C. Cl-MS m/z=245 (M+H). $^1$H NMR δ 7.35 (m, 1H,); 7.1 (dd, 1H); 6.8 (m, 1H); 6.5 (s, 2H); 3.7 (m, 1H); 3.6 (m, 1H); 2.9–2.6 (m, 5H); 2.6 (s, 3H); 1.8 (m, 2H). $[\alpha]^D$ −93.25°. Anal calcd for $C_{15}H_{17}FN_2 \cdot 1.5\ C_4H_4O_4$: C, 60.28; H, 5.54; N, 6.70. Found: C, 60.31; H, 5.67; N, 6.69.

Example 56

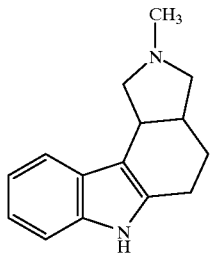

(±)-3aα,10cα-4,5,6,10c-Octahydro-2-methylpyrrolo[3,4-c]carbazole Fumarate 2-Propanolate [1:1.5:0.5]

Cpd. 56

A 0.96 mL sample of conc $H_2SO_4$ (18.2 mmol) was added slowly to 54.6 mL of 0.67M LAH in THF (36.4 mmol) at 0° C. under Ar. The solution was stirred for 30 min at 0° C. A solution of 1.85 g (7.27 mmol) under Ar. The solution was stirred for 30 min at 0° C. A 10.2 g (0.038 mol) sample of (±)-3aα,10cα-4,5,6,10c-tetrahydro-2-methylpyrrolo[3,4-c]carbazole-1,3-(2H,3aH)-dione in 15 mL of THF was added dropwise. The mixture was stirred at 0° C. for 0.5 h. A solution of 14.5 mL of 50% THF-water was added dropwise with cooling. The solid was filtered and washed with THF to give 1.5 g (91%) of (±)-3aα, 10cα-1,2,3,3a,4,5,6,10c-octahydro-2-methylpyrrolo[3,4-c]carbazole as a gum. A fumarate salt was prepared from 2-PrOH: mp 170–171° C. Cl-MS m/z=227 (M+H). $^1$H NMR (Me$_2$SO-d$_6$) δ 7.4 (d, 1H); 6.55 (s, 3H); 3.8 (t, 1H); 3.6 (q, 1H); 3.45 (m, 1H); 2.95 (m, 2H); 2.73 (m, 3H); 2.7 (s, 3H); 1.9 (m, 2H). Anal calcd. for $C_{15}H_{18}N_2 \cdot 1.5\ C_4H_4O_4 \cdot 0.05\ C_3H_8O$: C, 63.41; H, 6.09; N, 6.94. Found: C, 63.43; H, 6.16; N, 7.03.

Example 57

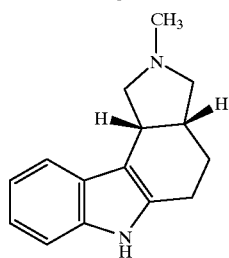

(S)-(+)-3aα,10cα-4,5,6,10c-Octahydro-2-methylpyrrolo[3,4-c]carbazole

Cpd. 57

A sample of (±)-3aα,10cα-1,2,3,3a,4,5,6,10c-octahydro-2-methylpyrrolo[3,4-c]carbazole was passed through a Chiralcel® OJ using hexane:EtOH:DEA 90.0%:10.0%:0.1% as the eluant. The first peak to elute was recrystallized from EtOAc. The absolute stereochemistry was established by single crystal x-ray diffraction analysis of a camphorsulfonic acid salt. mp 187–188° C. Cl-MS m/z= 227 (M+H). $^1$H NMR δ 7.85 (br s, 1H); 7.4 (d, 1H); 7.3 (d, 1H); 7.05 (m, 2H); 3.5 (q,1H); 3.4 (m, 1H) 3.1 (m, 1H); 2.65 (m, 3H); 2.4 (s,m, 4H); 2.25 (m, 1H); 1.85 (m, 2H). $[\alpha]^D$=+150°. Anal calcd for $C_{15}H_{18}N_2$: C, 79.61; H, 8.03; N, 12.38. Found: C, 79.27; H, 7.82; N, 12.14.

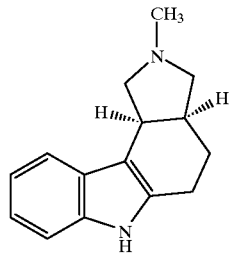

(R)-(−)-3aα,10cα-4,5,6,10c-Octahydro-2-methylpyrrolo[3,4-c]carbazole

Cpd. 58

The second peak from the foregoing example was recrystallized from EtOAc: mp 188–189° C. Cl-MS m/z=227 (M+H). ). $^1$H NMR δ 7.85 (br s, 1H); 7.4 (d, 1H); 7.3 (d, 1H); 7.05 (m, 2H); 3.5 (q, 1H); 3.4 (m, 1H); 3.1 (m, 1H); 2.65 (m, 3H); 2.4 (s, m, 4H); 2.25 (m, 1H); 1.85 (m, 2H). $[\alpha]^D$=−158°. Anal calcd for $C_{15}H_{18}N_2$: C, 79.61; H, 8.03; N, 12.38. Found: C, 79.43; H, 7.94; N, 12.11.

Example 59

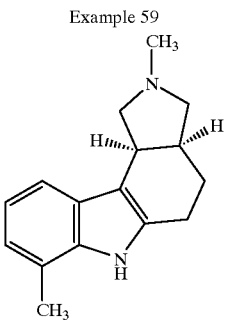

(−)-3aα,10cα-4,5,6,10c-Octahydro-2,7-
dimethylpyrrolo[3,4-c]carbazole Hydrochloride Cpd. 59

A 5.0 g sample of (±)-3aα,10cα,-1,2,3,3a,4,5,6,10c-octahydro-2,7-dimethylpyrrolo[3,4-c]carbazole (Cpd. 40) was passed through a Chiralcel® OJ column using hexane:EtOH:DEA 90%:10%:0.1% as the eluant. The first peak to elute was then flash chromatographed on silica gel (80:20:2 $CH_2Cl_2$:MeOH:$NH_4OH$) and converted to the HCl salt with 1.0 M HCl in $Et_2O$ to give 0.70 g of the pure enantiomer: mp 175° C. Cl-MS m/z=241 (M+H). $^1$H NMR δ 7.3–7.15 (m, 1H); 6.9 (m, 3H); 4.1 (m, 1H); 3.8 (m, 1H); 3.6–3.2 (m, 3H); 2.9–2.7 (m, 4H); 2.4 (s, 3H); 1.9 (m, 2H). $[α]^D = -102.4°$. Anal calcd for $C_{16}H_{20}N_2 \cdot HCl \cdot 0.33H_2O \cdot 0.5C_2H_6O \cdot 0.1\ C_3H_8O$: C, 66.72; H, 8.21; N, 9.02. Found: C, 66.46; H, 8.01; N, 8.88.

Example 60

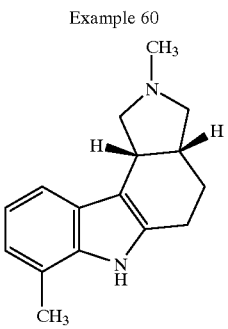

(±)-3aα,10cα-4,5,6,10c-Octahydro-2,7-
dimethylpyrrolo[3,4-c]carbazole Hydrochloride Cpd. 60

The second peak to elute from the foregoing example was subjected to flash chromatography on silica gel (80:20:2 $CH_2Cl_2$:MeOH:$NH_4OH$) and converted to the HCl salt with HCl 1.0 M in $Et_2O$ to give 0.44 g of the pure enantiomer: mp 173° C. Cl-MS m/z=241 (M+1). $^1$H NMR δ 7.3–7.15 (m, 2H); 6.9 (m, H); 4.1 (m, 1H); 3.8 (m, 1H); 3.6–3.2 (m, 3H); 2.9–2.7 (m, 4H); 2.4 (s, 3H); 1.9 (m, 2H). $[α]^D = +101.4$. Anal calcd for $C_{16}H_{20}N_2 \cdot HCl \cdot 0.33H_2O \cdot 0.25C_2H_6O$: C, 67.35; H, 7.93; N, 9.52. Found: C, 67.63; H, 7.96; N, 9.52.

Example 61

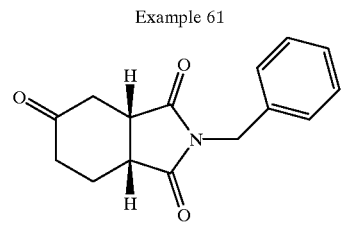

Tetrahydro-2-phenylmethyl-1H-isoindole-1,2,5-(2H,4H)-trione

Cpd. 61

A solution of 24.1 g (0.176 mol) of 2-trimethylsilyloxy-1,3-butadiene and 31.7 g (0.176 mol) of N-benzylmaleimide in 100 mL of benzene was heated under reflux overnight. The solvent was evaporated in vacuo to give a solid. To a solution of 59 g (0.186 mol) of this solid in 620 mL of $CH_2Cl_2$ was added 620 mL of 3 N aqueous HCl and the mixture was stirred at room temperature for 5 h. The $CH_2Cl_2$ layer was separated, dried ($MgSO_4$), and evaporated in vacuo to an oil. $^1$H NMR ($Me_2SO$-$d_6$) δ 7.3–7.0 (m, 5H); 4.5 (d, 2H); 3.45–3.3 (m, 1H); 3.22–3.12 (m, 1H); 2.72–2.48 (m, 3H); 2.28–1.78 (m, 3H).

Example 62

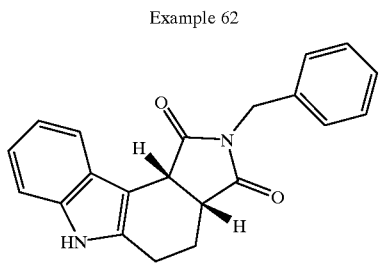

(±)-3aα,10cα-4,5,6,10c-Tetrahydro-2-
phenylmethylpyrrolo[3,4-c]carbazole-1,3-(2H,3αH)-dione Cpd. 62

A solution of 48 g (0.187 mol) of tetrahydro-2-phenylmethyl-1H-isoindole-1,3,5-(2H,4H)-trione and 18.3 mL (0.187 mol) of phenylhydrazine was heated under reflux for 2 h. The solution was cooled and the solid hydrazone (55 g) collected. The hydrazone was dissolved in a solution of 30 mL of concentrated $H_2SO_4$ in 160 mL of MeOH and heated under reflux for 1 h. The reaction mixture was added to $K_2CO_3$ solution, extracted into $CH_2Cl_2$, dried ($Na_2SO_4$) and concentrated. The residue was recrystallized from EtOAc, then flash chromatographed (14% EtOAc:43% $CH_2Cl_2$:43% hexane). Fractions containing the initial peak were evaporated to afford 14.4 g (23%) of (±)-3aα,10cα-4,5,6,10c-tetrahydro-2-phenylmethylpyrrolo[3,4-c]carbazole-1,3-(2H,3aH)-dione as a solid: $^1$H NMR ($CDCl_3$) δ 7.9.(m, 1H); 7.90 (s, 1H); 7.2 (m, 7H); 4.6 (q, 2H); 4.2 (d, 1H); 3.35 (m, 1H); 2.7 (m, 2H); 2.5 (m, 1H); 1.95 (m, 1H).

Example 63

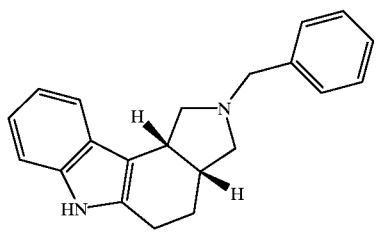

(±)-3aα,10c-Octahydro-2-phenylmethylpyrrolo[3,4-c]carbazole

Cpd. 63

A 6.78 g (0.13 mol) sample of conc. $H_2SO_4$ was added dropwise under Ar to a cooled solution of 381 mL (0.254 mol) of 0.67M LAH in THF so that the temperature did not exceed 10° C. The mixture was stirred at 0° C. for 0.5 h. A 14 g (0.042 mol) sample of (±)-3aα,10cα-4,5,6,10c-tetrahydro-2-phenylmethylpyrrolo[3,4-c]carbazole-1,3-(2H,3aH)-dione (cpd. 62) was added dropwise. The mixture was stirred at 0° C. for 1 h. A solution of 31 mL 50% $H_2O$ in THF was added dropwise with cooling. The solid was filtered and washed with THF to give 12 g (96%) of (±)-3aα,10cα-1,2,3,3a,4,5,6,10c-octahydro-2-phenylmethylpyrrolo[3,4-c]carbazole as a gum: $^1$H NMR (CDCl$_3$) δ 7.75 (s, 1H); 7.4 (d, 1H); 7.3 (m, 6H); 7.1 (m, 2H); 3.6 (s, 2H); 3.65 (m, 1H); 3.5 (m, 2H); 3.1 (m, 1H); 2.65 (m, 3H); 2.4 (t, 1H); 2.25 (m, 1H); 1.9 (m, 1H).

Example 64

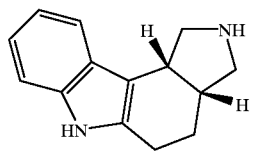

(±)-3aα,10cα-4,5,6,10c-Octahydropyrrolo[3,4-c]carbazole

Cpd. 64

A solution of 12.0 g (0.04 mol) of (±)-3aα,10cα-1,2,3,3a,4,5,6,10c-octahydro-2-phenylmethylpyrrolo[3,4-c]carbazole (cpd. 63) in 150 mL of HOAc was hydrogenated over 2.4 g of 10% palladium on carbon at 50 psi for 24 h. An additional 2.4 g of catalyst was added and the hydrogenation continued for 72 h. The catalyst was filtered and the acetic acid was evaporated. The residue was partitioned between $CH_2Cl_2$ and NaOH solution. The organic layer was dried ($K_2CO_3$) and concentrated. The residue was recrystallized from toluene to give 5.5 g (65%) of (±)-3aα,10cα-1,2,3,3a,4,5,6,10c-octahydropyrrolo[3,4-c]carbazole as a solid: mp 195–199° C. Cl-MS m/z=213 (M+H). $^1$H NMR (Me$_2$SO-d$_6$) δ 7.3 (d, 21H); 7.2 (d, 1H); 6.9 (m, 2H); 3.3 (m, 2H); 3.1 (m, 2H); 2.6 (m, 4H); 2.4 (m, 1H); 1.7 (m, 2H). Anal calcd. for $C_{14}H_{16}N_2$: C, 79.21; H, 7.60; N, 13.20. Found: C, 79.30; H, 7.58; N, 12.82.

Example 65

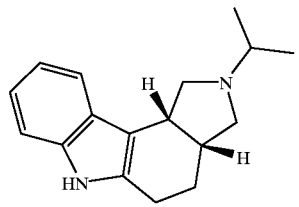

(±)-3aα,10cα-4,5,6,10c-Octahydro-2-(1-methylethyl)pyrrolo[3,4-c]carbazole Hydrochloride Hydrate [1.0:1.0:0.13]

Cpd. 65

To a solution of 0.82 g (3.83 mmol) of (±)-3aα,10cα-1,2,3,3a,4,5,6,10c-octahydropyrrolo[3,4-c]carbazole (cpd. 64) in 16 mL of 1,2-dichloroethane were added 0.62 mL (7.7 mmol) of acetone and 1.21 g (5.75 mmol) of sodium triacetoxyborohydride. The mixture was stirred for 2 h at 25° C. It was partitioned between $CH_2Cl_2$ and NaHCO$_3$ solution. The organic layer was dried ($K_2CO_3$) and concentrated. The residue was treated with ethereal HCl and the solid crystallized from 2-PrOH/Et$_2$O. There was obtained 0.92 g (81%) of (±)-3aα,10cα-1,2,3,3a,4,5,6,10c-octahydro-2-(1-methylethyl)pyrrolo[3,4-c]carbazole hydrochloride hydrate [1.0:1.0:0.13] as a greenish solid: mp 204–205° C. Cl-MS m/z 255 (M+H). $^1$H NMR (Me$_2$SO-d$_6$) δ 7.5 (7.5, 1H); 7.3 (d, 1H); 7.0 (m, 7H); 4.1 (m, 0.5H); 3.6 (m, 2H); 3.3 (m, 3H); 2.95 (m, 1H); 2.7 (m, 3H); 1.9 (m, 2H); 1.1 (m, 6H). Anal calcd. for $C_{17}H_{22}N_2$·1.0 HCl·0.13 $H_2O$: C, 69.64; H, 8.00; N, 9.55; $H_2O$, 0.79. Found: C, 69.24; H, 8.20; N, 9.14; $H_2O$, 0.43.

Example 66

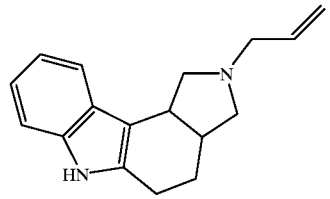

(±)-3aα,10cα-1,2,3,3a,4,5,6,10c-Octahydro-2-(propenyl)pyrrolo[3,4-c]carbazole Fumarate [1:0.6]

Cpd. 66

To a solution of 0.061 g (0.0029 mol) (±)-3aα,10cα-1,2,3,3a,4,5,6,10c-octahydropyrrolo[3,4-c]carbazole (cpd 64), 1.2 g (9 mmol) of $K_2CO_3$ in 15 mL of EtOH was added dropwise 0.25 mL (2.8 mmol) of allyl bromide. The reaction was stirred overnight. The reaction was partitioned between Et$_2$O and water, the organics were washed with water, brine and dried ($K_2CO_3$). The solvent was evaporated in vacuo. The residue was converted to the fumarate salt in 2-PrOH to give 0.2 g (23%) of a solid: mp 210–213° C. Cl-MS m/z=253 (M+H). $^1$H NMR (Me$_2$SO-d$_6$) δ 7.85 (d, 1H); 7.75 (d, 1H); 6.9 (m, 2H); 6.5 (s, 1H); 5.85 (m, 1H); 5.3–5.1 (m, 2H); 3.4 (m, 2H); 3.2 (m, 2H); 2.7–2.3 (m, 6H); 1.8 (m, 2H). Anal calcd for: $C_{17}H_{20}N_2$·0.6$C_4H_4O_4$: C, 72.11; H, 7.14; N, 8.52. Found: C, 71.93; H, 6.90; N, 8.49.

Example 67

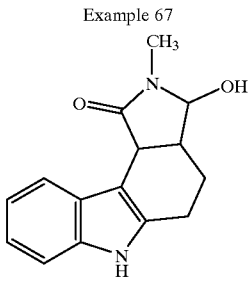

(±)-3aα,10cα-3,3a,4,5,6,10c-hexahydro-3-hydroxy-
2-methylpyrrolo-[3,4-c]carbazol-1 (H)-one Cpd. 67

A solution of 8.4 g (0.033 mol) of (±)-3aα,10cα-4,5,6, 10c-tetrahydro-2-methylpyrrolo[3,4-c]carbazole-1,3-(2H, 3aH)-dione in 150 mL of THF was cooled to −65° C. under Ar and 98 mL (0.098 mol) of 1M DIBAL in THF was added dropwise. The mixture was stirred 3 h at −65° C. A 21 mL sample of 50% MeOH in $H_2O$ was added. A 21 g sample of $Na_2SO_4$ was added. The mixture was diluted by the addition of MeOH/THF and stirred for 18 h. The solid was filtered and washed with MeOH/THF. The solvent was evaporated to give 8.2 g (97%) of (±)-3aα,10cα-3,3a,4,5,6,10c-octahydro-3-hydroxy-2-methylpyrrolo[3,4-c]carbazole-1 (H)-one as a white solid: Cl-MS m/z 257 (M+H). $^1$H NMR ($CDCl_3$) δ 7.7 (d, 1H); 7.2 (d, 1H); 6.9 (m, 2H); 5.2 (t, 1H); 3.7 (d, 1H); 2.9 (m, 1H); 2.6 (m, s, 5H); 1.9 (m, 1H); 1.75 (m, 1H).

Example 68

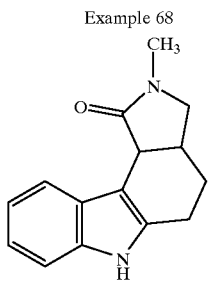

(±)-3aα,10cα-3,3a,4,5,6,10c-hexahydropyrrolo-2-
methyl [3,4-c]carbazol-1 (H)-one Cpd. 68

To a suspension of 8.12 g (0.032 mol) of (±)-3aα,10cα-3,3a,4,5,6,10c-octahydro-3-hydroxy-2-methylpyrrolo[3,4-c]carbazole-1 (H)-one in 180 mL of nitromethane were added sequentially 6.03 mL (0.0378 mol) of triethylsilane and 24.2 mL of TFA. The solid dissolved. The mixture was stirred at 25° C. for 1 h. It was poured into $Na_2CO_3$ solution and extracted with EtOAc. The organic solution was washed with brine, dried ($MgSO_4$) and concentrated. The residue was flash chromatographed (10% acetone in $CH_2Cl_2$) to give 3.5 g (46%) of (±)-3aα,10cα-2-methyl-3,3a,4,5,6,10c-hexahydropyrrolo[3,4-c]carbazol-1 (H)-one as a solid: Cl-MS m/z=241 (M+H). $^1$H NMR ($CDCl_3$) δ 8.0 (m, 1H); 7.75 (s, 1H); 7.2 (m, 2H); 7.1 (m, 2H); 3.85 (d, 1H); 3.55 (m, 1H); 3.2 (m, 1H); 2.85 (s, 3H); 2.75 (m, 3H); 2.0 (m, 2H).

Example 69

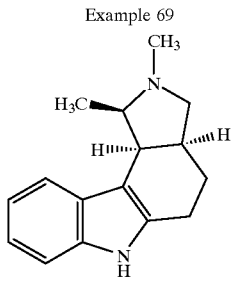

(±)-1α,3aβ,10cβ-1,2,3,3a,4,5,6,10c-Octahydro-1,2-
dimethylpyrrolo-[3,4-c]carbazole Cpd. 69

A 135 mL sample of 0.36 M methyllithium in $Et_2O$ (49 mmol) was cooled to 0° C. under Ar and 2.35 g (9.8 mmol) of (±)-3aα,10cα-3,3a,4,5,6,10c-hexahydro-2-methylpyrrolo [3,4-c]carbazol-1 (H)-one was added. The mixture was stirred at 25° C. for 16 h. A solution of 39 mL of 1 M LAH in THF (39 mmol) was added and the mixture stirred for 2 h. The mixture was cooled and 4.4 mL of $H_2O$, 1.5 mL of 3N NaOH and 1.5 mL of $H_2O$ were added sequentially. The solid was filtered and washed with THF. The filtrate was concentrated and chromatographed on a Waters Prep 500, using $CH_2Cl_2$: $MeOH:NH_4OH$; 92:8:0.8 as eluant. The first peak was collected. There was obtained 1.24 g (52%) of (±)-1α,3aβ,10cβ-1,2,3,3a,4,5,6,10c-octahydro-1,2-dimethylpyrrolo[3,4-c]carbazole as a white solid: mp 172–173° C. Cl-MS m/z=241 (M+H). $^1$H NMR ($CDCl_3$) δ 7.75 (s, 1H); 7.45 (d, 1H); 7.3 (m, 1H); 7.1 (m, 2H); 3.6 (t, 1H); 2.9 (m, 2H); 2.7 (m, 3H); 2.4 (m, s, 4H); 1.9 (m, 2H); 0.9 (d, 3H).

Example 70

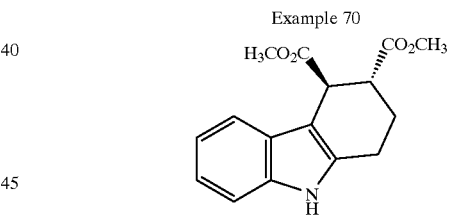

(±)-trans-Dimethyl-1,2,3,4-tetrahydro[9H]carbazole-
3,4-dicarboxylate

Cpd. 71

A solution of 4.5 g (0.035 mol) 2-ethenyl-1H-indole, 5.4 g (0.042 mol) and dimethyl fumarate in 50 mL of xylene was placed into a pressure bottle and heated to 100° C. overnight. After cooling, the reaction mixture was poured into water and $Et_2O$ was added. The organics were washed with water and brine, and dried ($Na_2SO_4$). The $Na_2SO_4$ was filtered and the filtrate was cooled at 0° C. The solid was collected and recrystallized from EtOAc to give 3.6 g of a white solid (36%): mp 133–135° C. Cl-MS m/z=287 (M+H). $^1$H NMR ($CDCl_3$) δ 7.85 (bd s, 1H); 7.6 (d, 1H); 7.0–7.3 (m, 3H); 4.3 (d, 1H); 3.65 (s, 3H); 3.75 (s, 3H); 3.35 (m, 1H); 2.8 (m, 1H); 2.4 (s, 1H); 2.1 (m, 1H). Anal calcd for: $C_{16}H_{17}N_2O_4$: C, 66.89; H, 5.96; N, 4.88. Found: C, 66.73; H, 5.95; N, 4.83.

Example 71

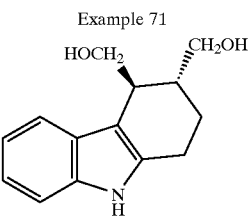

(±)-trans-1,2,3,4-tetrahydro-bis(3,4-hydroxymethyl)[9H]carbazole

Cpd. 71

A solution of 8.72 g (0.03 mol) of trans-dimethyl-1,2,3,4-tetrahydro[9H]carbazole-3,4-dicarboxylate in an 80:20 mixture of THF:Et$_2$O was added dropwise to a suspension of 5.7 g (0.15 mol) LAH in 100 mL of Et$_2$O. After stirring for 3 h, 5.7 mL of water, 17.1 mL of 3N NaOH and 5.7 mL of water were added carefully. The suspension was stirred for one hour and the solid was filtered off. The filtrate was washed with water, brine and dried (Na$_2$SO$_4$). The solvent was evaporated in vacuo to give 5.23 g (75%) of a white solid: mp 129–131° C. MS-Cl m/z=232 (M+H). $^1$H NMR (CDCl$_3$) δ 7.4 (d, 1H); 7.25 (d, 1H); 6.85–7.0 (m, 2H); 4.7 (t, 1H); 4.5 (t, 1H); 3.75 (m, 1H); 2.6 (s, 1H); 2.25 (m, 1H); 1.0 (m, 2H). Anal calcd for: C$_{14}$H$_{17}$NO$_2$: C, 72.70; H, 7.41; N, 6.06. Found: C, 72.52; H, 7.38; N, 5.92.

Example 72

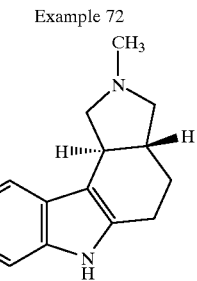

(±)-3aα,10cβ-1,2,3,3a,4,5,6,10c-Octahydro-2-methylpyrrolo-[3,4-c]carbazole Fumarate [1.0:0.55]

Cpd. 72

A solution of 2.2 g (9.5 mmol) of (±)-trans-1,2,3,4-tetrahydydro-bis(3,4-hydroxymethyl)[9H]carbazole, 25 mL of CH$_2$Cl$_2$ and 2.5 mL (0.020 mol) triethylamine was cooled in an ice bath. A solution of 1.5 mL of methanesulfonyl chloride (0.020 mol) in 10 mL of CH$_2$Cl$_2$ was added dropwise. The solution was stirred at room temperature overnight. The reaction mixture was poured into NaHCO$_3$, the organics were washed with water, brine and dried (Na$_2$SO$_4$). The solvent was evaporated in vacuo. The residue was taken up in 15 mL of MeOH and placed into a pressure bottle with 23 mL (0.046 mol) of 2.0M methylamine in MeOH. The bottle was sealed and heated to 80° C. overnight. The solvent was evaporated in vacuo. The residue was partitioned between Et$_2$O and 3N NaOH. The organics were washed with water and brine, and dried (K$_2$CO$_3$). The solvent was evaporated in vacuo. The residue flash chromatographed on silica gel (80:20:2 CH$_2$Cl$_2$:MeOH:NH$_4$OH). The oil was converted to the fumarate salt in 2-PrOH to give 0.21 g (9%) of a white solid; 190° C. (d). Cl-MS m/z=227 (M+H). $^1$H NMR (Me$_2$SO-d$_6$) δ 7.4 (d, 1H); 7.3 (d, 1H); 7.1–6.9 (m, 2H); 6.5 (s, 1.2 H); 3.8 (m, 1H); 3.25 (m, 2H); 3.1 (m, 1H); 2.9–2.6 (m, 4H); 2.6 (s, 3H); 1.9 (m, 1H); 1.65 (m, 1H). Anal calcd for: C$_{15}$H$_{18}$N$_2$•C$_4$H$_4$O$_4$: C, 63.66; H, 6.43; N, 7.04. Found: C, 63.66; H, 6.20; N, 7.11.

Example 73

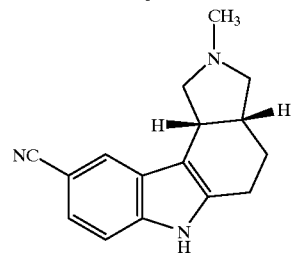

(±)-3aα,10cα-1,2,3,3a,4,5,6,10c-Octahydro-9-cyano-2-methylpyrrolo-[3,4-c]carbazole Cpd. 73

Into a pressure bottle was placed a solution of 4.6 g (0.015 mol) of (±)-1a, 3aα,10cα-1,2,3,3a,4,5,6,10c-octahydro-9-bromo-2-methylpyrrolo[3,4-c]carbazole (cpd. 5), 20 mL of pyridine, and 2.0 g (0.030 mol) of copper cyanide. Argon was bubbled through the solution for 10 m then 0.86 g (0.75 mmol) of tetrakistriphenylphosphine palladium (0) was added and the bottle capped and heated to 120° C. for 5 days. Et$_2$O and NH$_4$OH were added. After stirring for 10 m, the organics were separated and washed with dilute NH$_4$OH, water, brine and dried (Na$_2$SO$_4$). The solvent was evaporated in vacuo. The residue was flashed chromatographed on silica gel (80:20:2 CH$_2$Cl$_2$:MeOH:NH$_4$OH). The product from the chromatography was crystallized from t-butyl methyl ether. The resulting solid was extracted with hot t-butyl methyl ether and the solvent was evaporated in vacuo. This residue was converted to the fumarate salt and recrystallized from 2-PrOH to give 0.55 g of a white solid (12%): mp 235–237° C. MS-Cl m/z=252 (M+H). $^1$H NMR (Me$_2$SO-d$_6$) δ 7.9 (s, 1H); 7.35 (q, 2H); 6.5 (s, 1H); 3.4 (m, 2H); 3.1 (m, 1H); 2.7 (m, 2H); 2.4 (s, 3H); 1.8 (m, 2H). Anal calcd for: C$_{16}$H$_{17}$N$_3$•0.55 C$_4$H$_4$O$_4$: C, 69.36; H, 6.14; N, 13.33. Found: C, 69.19; H, 6.20; N, 13.36.

Example 74

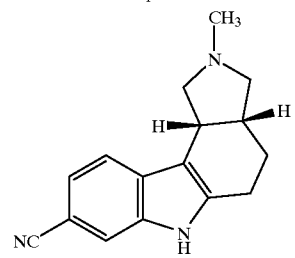

(±)-3aα,10cα-1,2,3,3a,4,5,6,10c-Octahydro-8-cyano-2-methylpyrrolo-[3,4-c]carbazole Cpd. 74

Cpd. 74 was prepared using the procedure of Example 73 and employing (±)-1a, 3aα,10cα-1,2,3,3a,4,5,6,10c-octahydro-8-bromo-2-methylpyrrolo[3,4-c]carbazole 9-bromo-2-methylpyrrolo[3,4-c]carbazole (cpd. 17) instead of (±)-1α,3aβ,10cα-1,2,3,3a,4,5,6,10c-octahydro-9-bromo-2-methylpyrrolo[3,4-c]carbazole, to give (±)-3aα,10cα-1,2,3,3a,4,5,6,10c-octahydro-8-cyano-2-methylpyrrolo[3,4-c]carbazole:mp 190–193° C. Cl-MS m/z=252 (M+H). ¹H NMR (Me₂SO-d₆) δ 7.7 (br s,1H); 7.5 (d, 1H); 7.3 (d, 1H); 6.5 (s, 3H); 3.5 (m, 2H); 3.3 (m, 1H); 2.7 (m, 4H); 2.55 (m, 3H); 2.5 (m, 1H); 1.85 (m, 2H).

Example 75

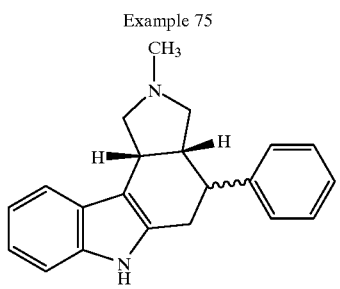

(±)-3aα,10cα-1,2,3,3a,4,5,6,10c-Octahydro-2-methyl-4-phenylpyrrolo-[3,4-c]carbazole Fumarate [1.0:0.55]

Cpd. 75

A solution of 56 mL (0.056 mol) of LAH in THF was cooled in an ice bath. A 1.47 mL (0.028 mol) sample of H₂SO₄ was added dropwise controlling the temperature below 12° C. The resulting solution was stirred at 0° C. for 30 m. A solution of 3.1 g (9 mmol) of 4,5,6,10c-tetrahydro-2-methyl-4-phenylpyrrolo[3,4-c]carbazole-1,3-(2H,3aH)-dione (cpd. 28) in 20 mL of THF was added dropwise and stirred for 1.5 h at 0° C. A solution of 12 mL of 50:50 THF:water added dropwise and stirring continued for 1 h. The solid was filtered off. The filtrate was washed with water, brine and dried (Na₂SO₄). The solvent was evaporated in vacuo. The residue was passed through a flash chromatography column using silica gel (90:10:1 CH₂Cl₂:MeOH:NH₄OH). The resulting oil was converted to the fumarate salt in 2-PrOH and recrystallized from EtOH to give 0.36 g (11%) of the product: ¹H NMR (CDCl₃) δ 7.1–6.9 (m, 2H); 6.5 (s, 1H); 3.7 (m, 1H); 3.5–3.15 (m, 3H); 3.0 (m, 1H); 2.8 (dd, 1H); 2.75–2.6 (m, H); 2.4 (m, 1H); 2.3 (s, 3H). Anal calcd for: C₂₁H₂₂N₂•0.55 C₄H₄O₄: C, 76.00; H, 6.60; N, 7.65. Found: C, 76.00; H, 6.50; N, 7.58.

Example 76

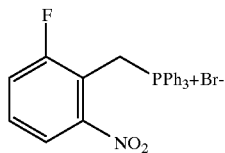

[(6-Fluoro-2-nitrophenyl)methyl]triphenylphosphonium Bromide

Cpd. 76

Cpd. 76 was prepared in 76% yield by the method of Example 21 where 2-nitro-6-fluorobenzyl bromide was used in place of 2-nitro-4-fluorobenzyl bromide.

Example 77

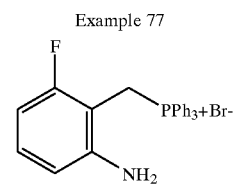

[(2-Amino-6-fluorophenyl)methyl]triphenylphosphonium Bromide

Cpd. 77

Cpd 77 was prepared in 44% yield using the method of example 22 and reducing cpd. 76 in place of cpd 22.

Example 78

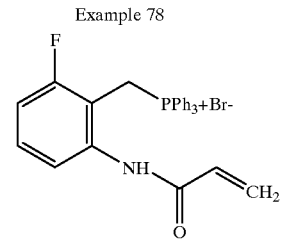

[[6-Fluoro-2-[(1-oxo-2-propenyl)amino]phenyl]methyl]triphenylphosphonium Bromide Cpd. 78

Cpd. 78 was prepared in 73% yield using the method of example 23 by replacing Cpd. 22 with Cpd. 77.

Example 79

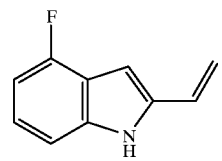

2-Ethenyl-4-fluoro-1H-indole

Cpd. 79

Cpd. 79 was prepared in the manner of example 24 by using cpd. 78 in place of cpd. 23 to give 12.6 g (93%) of 2-ethenyl-4-fluoro-1H-indole as an oil. Cl-MS m/z=162 (M+H). ¹H NMR (CDCl₃) δ 7.1 (m, 2H); 6.7–6.8 (m, 2H); 6.55 (s, 1H); 5.6 (d, 1H); 5.3 (d, 1H).

Example 80

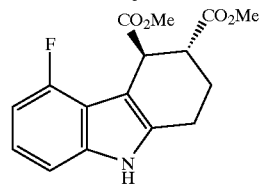

(±)-trans-Dimethyl 1,2,3,4-tetrahydro-10-fluoro[9H]carbazole-3,4-dicarboxylate

Cpd. 80

Cpd. 80 was prepared following the method of example 70 and replacing 2-ethenyl-1H-indole with Cpd. 79.

Example 81

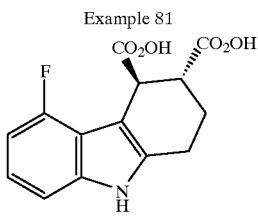

(±)-trans-1,2,3,4-tetrahydro-10-fluorobis(3,4-hydroxymethyl)[9H]carbazole

Cpd. 81

Cpd. 81 was prepared by the method of example 71 by replacing cpd. 70 with cpd. 80.

Example 82

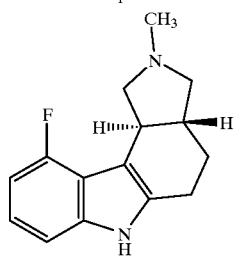

(±)-3aα,10cβ-1,2,3,3a,4,5,6,10c-Octahydro-10-fluoro-2-methylpyrrolo-[3,4-c]carbazole Oxalate [1:1]

Cpd. 82

Cpd. 82 was prepared using cpd. 81 as the starting material and the method of example 72 to give (±)-3aα,10cβ-1,2,3,3a,4,5,6,10c-octahydro-10-fluoro-2-methylpyrrolo[3,4-c]carbazole in 5% yield as the oxalate salt mp. 188° C. (decomp). Cl-MS m/z=245 (M+H). $^1$H NMR (Me$_2$SO$_4$-d$_6$) δ 7.1 (m, 1H); 7.0 (m, 1H); 6.7 (m, 1H); 4.1 (m, 1H); 4.0 (m, 1H); 3.8–3.6 (m, 2H); 2.95–3.2 (m, 3H); 2.8 (s, 3H); 2.75 (m, 2H); 2.0 (m, 1H); 1.7 (m, 1H).

Example 83

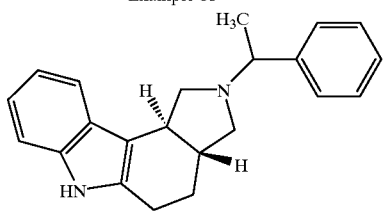

3aα,10cβ-1,2,3,3a,4,5,6,10c-Octahydro-2-(α-phenylethyl)pyrrolo-[3,4-c]carbazole

Cpd. 83

A solution of 16.5 mL (2.2 eq) of mesyl chloride in 200 mL of CH$_2$Cl$_2$ was added dropwise to a solution of 22.7 g (0.098 mol) trans-1,2,3,4-tetrahydrobis(3,4-hydroxymethyl)[9H]carbazole (cpd. 71), 29.5 mL of triethylamine (2.2 eq) in 200 mL of CH$_2$Cl$_2$ at 0° C. The reaction was stirred overnight. The reaction mixture was poured into ice/NaHCO$_3$, the organics were separate off, washed with H$_2$O, brine and dried (Na$_2$SO$_4$). The solvent was evaporated in vacuo. The residue was taken up in 250 mL EtOH, 37.3 mL (7 eq) of (S)-α-methylbenzylamine was added and the reaction was refluxed overnight. The solvent was evaporated in vacuo. The residue was taken up in Et$_2$O, washed with H$_2$O, brine and dried (Na$_2$SO$_4$). The solvent was evaporated in vacuo. The residue was passed through a Biotage Flash 75® on silca gel with 90:10:1 CH$_2$Cl$_2$:MeOH:NH$_4$OH to separate the diastereomers. They were recrystallized from EtOAc to give 6.0 g of (+)-3aα,10cβ-1,2,3,3a,4,5,6,10c-octahydro-2-(α-methylphenylethyl)pyrrolo[3,4-c]carbazole and 6.0 g of (−)-3aα,10cβ-1,2,3,3a,4,5,6,10c-octahydro-2-(α-methylphenylethyl)pyrrolo[3,4-c]carbazole. mp of peak one 154–157° C. mp of second peak 115–119° C. MS-Cl m/z=317 (M+H). $^1$H NMR (peak 1) (CDCl$_3$) δ 7.8 (bs, 1H); 7.4–7.2 (m, 9H); 7.1 (m, 2H); 3.7 (m, 2H); 2.9 (m, 4H); 2.75 (dd, 2H); 2.65 (t, 1H); 2.15 (m, 1H); 2.0 (m, 1H); 1.4 (d, 3H). $^1$H NMR (peak 2) (CDCl$_3$) d 7.8 (bs, 1H); 7.4–7.2 (m, 9H); 7.1 (m, 2H); 3.7 (d, 1H); 3.5 (d, 1H); 3.0–2.85 (m, 4H); 2.8 (d, 1H); 2.65 (t, 1H); 2.15 (m, 1H); 1.9 (m, 1H); 1.55–1.7 (m, 2H); 1.5 (d, 3H).

Example 84

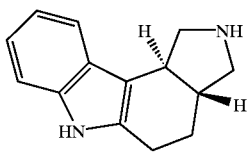

(±)-3aα,10cβ-1,2,3,3a,4,5,6,10c-Octahydropyrrolo-[3,4-c]carbazole

Cpd. 84

A solution of 6.0 g (0.0188 mol) of (+)-3aα,10cβ-1,2,3,3a,4,5,6,10c-octahydro-2-(α-methylphenylethyl)pyrrolo[3,4-c]carbazole (peak 1) in 100 MeOH was placed into a Parr® bottle over 2.0 g of Pearlman's catalyst. The bottle was placed on a Parr® shaker under 50 psi of H$_2$ at 60° C. and shaken for 4.5 h. The catalyst was filtered off and the solvent was evaporated in vacuo to give (+)-3aα,10cβ-1,2,3,3a,4,5,6,10c-octahydropyrrolo[3,4-c]carbazole of a glass. MS-Cl m/z=213 (M+H). $^1$HNMR (CDCl$_3$) d 7.35 (m,s, 3H); 7.05 (m, 2H); 3.9 (m, 1H); 3.4 (m, 2H); 3.25 (m, 2H); 2.9 (m, 4H); 2.85 (m, 2H).

Example 85

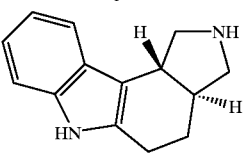

(−)-3aα,10cβ-1,2,3,3a,4,5,6,10c-Octahydropyrrolo-[3,4-c]carbazole

Cpd. 85

Cpd. 85 was produced as a glass by the method of example 84 using 6.0 g of peak 2 from example 82. MS-Cl m/z=213 (M+H).

Example 86

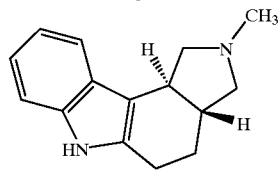

(±)-3aα,10cβ-1,2,3,3a,4,5,6,10c-Octahydro-2-methylpyrrolo-[3,4-c]carbazole Fumarate [1:1]

Cpd. 86

A solution of 2.82 g (0.013 moles) of 3aα,10cβ-1,2,3,3a,4,5,6,10c-octahydropyrrolo[3,4-c]carbazole (cpd. 83), 0.46 mL (1.2 eq) of 37% formalin in 50 mL of MeOH was stirred for 1 h. To this was added 0.38 g (0.01 moles) $NaBH_4$ and the reaction was stirred overnight under argon. 3N HCl was added and the reaction was stirred for 40 m. After concentrating the solvent in vacuo the residue was partitioned between $Et_2O$ and, 3N NaOH. The organics were washed with $H_2O$, brine and dried ($Na_2SO_4$). The solvent was evaporated in vacuo. The residue was passed through a Biotage Flash 40® on silica gel, 90:10:1 $CH_2Cl_2$:MeOH:$NH_4OH$. The product was converted to the fumarate salt in 2-PrOH to give 1.59 g (24%) of a white solid. mp. 213–215° C. MS-Cl m/z=227 (M+H). $^1$H NMR ($Me_2SO_4$-$d_6$) δ 7.35–7.25 (Ar, 2H); 7.05–6.9 (Ar, 2H); 6.5 (s, 2H); 4.0(bs, 1H); 3.35 (m, 2H); 3.0–2.8 (m, 4H); 2.8 (s, 3H);2.2–2.0 (m, 2H); 1.7 (m, 1H). Anal calcd for $C_{15}H_{18}N_2 \cdot C_4H_4O_4 \cdot 0.02\ H_2O$: C, 66.58; H, 6.48; N, 8.17. Found: C, 66.23; H, 6.33, N, 7.97; KF 0.1.

Example 87

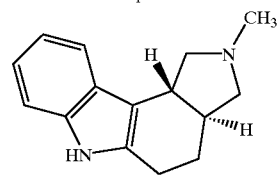

(−)-3aα,10cβ-1,2,3,3a,4,5,6,10c-Octahydro-2-methylpyrrolo-[3,4-c]carbazole Fumarate [1:0.5]

Cpd. 87

Compound 87 was produced in 47% yield by the method of Example 86 using cpd 84 as a starting material:mp 263–268° C. (decomp.). MS-Cl m/z=227 (M+H). $^1$H NMR ($Me_2SO_4$-$d_6$) d 7.35–7.25 (Ar, 2H); 7.05–6.9 (Ar, 2H); 6.5 (s, 1H); 3.7 (bt, 1H); 3.15 (bt, 1H); 2.9 (m, 5H); 2.7 (s, 3H); 2.2–2.1 (m, 1H); 2.0 (m, 1H); 1.15 (m, 1H). Anal calcd. for $Cl_{15}H_{18}N_2 \cdot 0.5C_4H_4N_4$: C, 71.81; H, 7.09; N, 9.85. Found:C, 71.49; H, 7.11; N, 9.72.

Example 88

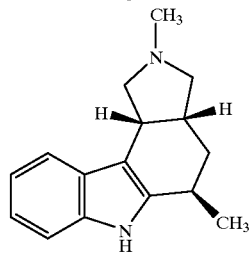

(±)-3aα,5α,10cα-4,5,6,10c-Octahydro-2,5-dimethylpyrrolo[3,4-c]carbazole

Cpd. 88

Cpd. 88 was prepared from Cpd. 26 by the method essentially described in Example 30. Cl-MS m/z=241 (M+H). HNMR ($MeSO_4$-$d_6$) δ 7.35 (d,1H); 7.3 (d, 1H); 7.1–6.85 (m, 2H); 6.5 (s, 1H); 3.45–3.2 (m,4H); 2.85 (m, 1H); 2.6–2.4 (m, 5H); 1.9 (m,1H); 1.5–1.35 (q, 1H); 1.3 (d, 3H). Anal calc'd for: $C_{16}H_{20}N_2 \cdot C_4H_4O_4$: C, 72.46; H,7.43, N,9.39. Found: C,71.61; H,7.43; N,9.12.

Example 89

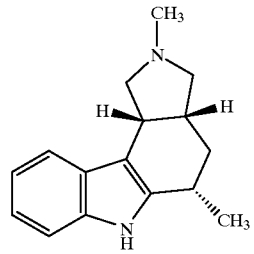

(±)-3aα,5β,10cα-4,5,6,10c-Octahydro-2,5-dimethylpyrrolo[3,4-c]carbazole

Cpd. 89

Cpd. 89 was prepared from Cpd. 27 by the method essentially described in Example 30. Cl-MS m/z=241 (M+H). HNMR ($MeSO_4$-$d_6$) δ 7.35 (d,1H); 7.3 (d, 1H); 7.1–6.85 (m, 2H); 6.5 (s, 1H); 3.4 (m, 3H); 3.1 (m, 1H); 2.9 (m, 1H); 2.75 (m, 1H); 2.4 (s, 3H); 1.9 (m,1H); 1.55 (m,1H); 1.3 (d, 3H). Anal calc'd for: $C_{16}H_{20}N_2 \cdot C_4H_4O_4 \cdot 0.68\ C2H6O$: C, 70.53; H, 7.97; N,8.50. Found: C, 70.27; H, 7.74; N, 8.42.

BIOLOGICAL EXAMPLES

The biological activity of the compounds of the invention was demonstrated by in vivo and in vitro assays. The ability of select compounds of the invention to bind to the $α_1$, and the $α_2$-adrenergic receptors was demonstrated by comparing the amount of bound radiolabeled ligand in the presence and absence of test compounds.

Example 90

The $α_1$-adrenergic activity was demonstrated in the following in vitro assay. Charles River male Wistar (virus-free) rats were group housed for approximately one week and given food and water (Wayne Lab Blox) ad libitum. Animals were exposed to equal hours(12—12) of dark and light and used at a weight range of 150–280 g (8 to 10 weeks of age). Rats were sacrificed by cervical dislocation and their brains were rapidly excised and immediately placed on ice. The cortex was removed, weighed, and used immediately or frozen on dry ice.

The frozen tissue was homogenized in 20 volumes of HEPES buffered sucrose (10 mM HEPES, 300 mM sucrose, pH 7.5) using a motor driven Teflon pestle/glass homogenizer (all homogenates and solutions were maintained at 4–8° C.). The homogenate was centrifuged at 1000×g for 10 minutes, and the supernatant was recentrifuged at 48,000×g for 10 min. The sediment ($P_2$ fraction) was resuspended in 30 volumes of phosphate buffer (3 mM $K_2HPO_4$-$KH_2PO_4$ pH 7.4). This suspension was preincubated at 25° C. for 30 min, then recentrifuged as above. The pellet was resuspended in 30 volumes of phosphate buffer to form a membrane suspension which was kept on ice.

Test samples comprised, 1.45 mL of the phosphate buffer, 0.1 ml $H_2O$, 0.1 mL of the test compound (1 mg, dissolved in an appropriate volume of water or diluted DMSO) or water (used for total bound Dpm) or norepinephrine (used to determine nonspecific binding at a final conc. of 1 uM), 0.1 mL of $^3H$-prazosin (NEN) at a final concentration of 0.05 nM in phosphate buffer ($^3H$-prazosin concentration used is at or below the $K_d$), and 0.25 mL of the membrane suspension. The samples were incubated in a 25° C. water bath for 20 min, harvested on a Brandel Cell Harvester on to Wallac filtermat-B sheets (96 sample format), washed three times with 2 mL cold HEPES-buffer (10 mM, pH 7.5), and dried in a microwave oven. To each sample area 80 ul of Betaplate Scint scintillation fluid (LKB) was added and analyzed on a LKB (Wallac) 1205 BetaPlate liquid scintillation counter.

The data were used to calculate either the % inhibition compared to control binding (a single concentration of test compound is evaluated) or a $K_i$ value (a range of concentrations are tested). The background is subtracted from mean cpm values and % inhibition is calculated as follows:(test compound dpm -nonspecific dpm)/(total dpm-nonspecific dpm)*100. $K_i$ values are calculated using the LIGAND (Munson, P. J. and Rodbard, D.: LIGAND: a versatile computerized approach for characterization of ligand-binding systems. Anal. Biochem. 107: 220–239, 1980.) data analysis program. Compound 58 has a $K_i$ of 61 nM.

The $\alpha_2$-adrenergic activity of the compounds was determined by the following in vitro assay. Male, Wistar rats (150–250 g, VAF, Charles River, Kingston, N.Y.) were sacrificed by cervical dislocation and their brains removed and immediately placed in ice cold HEPES buffered sucrose. The cortex was dissected out and homogenized in 20 volumes of HEPES sucrose in a Teflon®-glass homogenizer. The homogenate was centrifuged at 1000×g for 10 min, and the resulting supernatant centrifuged at 42,000×g for 10 min. The resulting pellet was resuspended in 30 volumes of 3 mM potassium phosphate buffer, pH 7.5, preincubated at 25° C. for 30 min and recentrifuged. The resulting pellet was resuspended as described above and used for the receptor binding assay. Incubation was performed in test tubes containing phosphate buffer, 2.5 mM $MgCl_2$, aliquots of the synaptic membrane fraction, the ligand $^3H$-para-aminoclonidine and test drug at 25° C. for 20 min. The incubation was terminated by filtration of the tube contents through glass fiber filter sheets. The sheets were washed with 10 mM HEPES buffer and the adhering radioactivity was quantified by liquid scintillation spectrometry.

Dose-response data are analyzed with LIGAND, a non-linear curve fitting program designed specifically for the analysis of ligand binding data. This assay is described by Simmons, R. M. A., and Jones, D. J., Binding of [$^3H$-] prazosin and [$^3H$-]p-aminoclonidine to α-Adrenoceptors in Rat Spinal Cord, Brain Research 445: 338–349, 1988. Compound 58 has a $K_i$, of 9.4 nM.

The analgesic activity of compounds of Formula I were determined in the following in vivo assay. The procedure was run essentially as described by H. Collier et al. in B. J. Pharmacol. Chemother., 32: 295–310, 1968, with minor modifications. Mice (Male, Cr1:CD-1, Charles River Laboratories) were used in the following example. The test drugs or appropriate vehicle were administered orally (10 mL/kg, p.o.) or subcutaneously (10 mL/kg, s.c.) and 30 minutes later the animal received an intraperitoneal (i.p.) injection of 5.5 mg/kg acetylcholine bromide. The mice were then placed in glass bell jars and observed for a ten minute observation period for the occurrence of an abdominal constriction response (defined as a wave of constriction and elongation passing caudally along the abdominal wall, accompanied by a twisting of the trunk and followed by extension of the hind limbs). The percent inhibition of this response to antinociceptive stimulus (equated to % analgesia) was calculated as follows: The % inhibition of response, i.e., % analgesia is equal to the number of non-responding drug-treated animals×100 divided by the number of animals in the group.

The $ED_{50}$ values and their 95% fiducial limits were determined by a computer assisted probit analysis. An analgesic effect was observed for Compound 58 at 15 min after oral dosing. This effect lasted for 4–5 hours. $ED_{50}$ values of 5.8 and 5.4 were obtained for Compound 58 and tramadol respectively.

Table A lists the % inhibition for some compounds of the invention. Unless otherwise indicated the compounds were administered s.c. at 30 mg/kg.

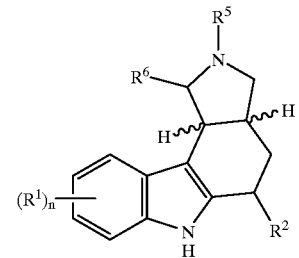

TABLE A

| # | $R^1$ | $R^2$ | $R^5$ | $R^6$ | ring junction | % inhibition @ 30 mg/kg |
|---|---|---|---|---|---|---|
| 57 | H | H | $CH_3$ | H | cis | 100 |
| 58 | H | H | $CH_3$ | H | cis | 100 po |
| 31 | 9-F | H | $CH_3$ | H | cis | 93 |
| 32 | 7-$OCH_3$ | H | $CH_3$ | H | cis | 100 |
| 64 | H | H | H | H | cis | 80 |
| 34 | 7,8-di$CH_3$ | H | $CH_3$ | H | cis | 100 |
| 35 | 7-Cl | H | $CH_3$ | H | cis | 93 |
| 36 | 9-Br | H | $CH_3$ | H | cis | 100 |
| 37 | 8-Cl | H | $CH_3$ | H | cis | 100 |
| 38 | 10-Cl | H | $CH_3$ | H | cis | 87 po |
| 40 | 7-$CH_3$ | H | $CH_3$ | H | cis | 87 po |
| 41 | 8-$CF_3$ | H | $CH_3$ | H | cis | 100 |
| 42 | 10-$CF_3$ | H | $CH_3$ | H | cis | 60 |
| 73 | 9-CN | H | $CH_3$ | H | cis | 100 |
| 65 | H | H | 2-Pr | H | cis | 93 po |

TABLE A-continued

| # | R¹ | R² | R⁵ | R⁶ | ring junction | % inhibition @ 30 mg/kg |
|---|---|---|---|---|---|---|
| 66 | H | H | allyl | H | cis | 100 |
| 53 | H | H | t-Bu | H | cis | 100 |
| 32 | 7-OCH₃ | H | CH₃ | H | cis | 100 |
| 30 | 8-F | H | CH₃ | H | cis | 100 po |
| 44 | 10-F | H | CH₃ | H | cis | 100 po |
| 45 | 7-Br | H | CH₃ | H | cis | 73 |
| 46 | 7-Et | H | CH₃ | H | cis | 100 |
| 47 | 7-F | H | CH₃ | H | cis | 93 po |
| 48 | 7-CF₃ | H | CH₃ | H | cis | 100 |
| 49 | 8,10-diCH₃ | H | CH₃ | H | cis | 100 |
| 50 | 8,10-diF | H | CH₃ | H | cis | 100 |
| 33 | 7,10-diCl | H | CH₃ | H | cis | 33 |
| 39 | 9-(2-Pr) | H | CH₃ | H | cis | 27 |
| 69 | H | H | CH₃ | CH₃ | cis | 100 |
| 72 | H | H | CH₃ | H | trans | 100 po |
| 75 | H | 4-Ph | CH₃ | H | cis | 100 |
| 88 | H | cis-5-CH₃ | CH₃ | H | cis | 93 po |
| 89 | H | trans-5-CH₃ | CH₃ | H | cis | 100 |

Example 91

The analgesic activity was determined in another model using rats as the test animal. The procedure was essentially described by P. VonVoightlander et al. in Air-induced Writhing, a Rapid Broad Spectrum Assay for Analgesics, *Drug Dev. Res.*, 2, 577–81, (1982). The test compound or vehicle was administered p.o. (2 mL/kg) and after 30 min, the animals received an i.p. injection of air (10 mL). The animals were placed into individual observation chambers and observed for 30 min for the occurrence of abdominal constriction as defined above. The percent inhibition of this response was calculated as follows. The % inhibition of response, i.e., % analgesia is equal to the number nonresponding drug-treated animals×100 divided by the number of animals in the group. An analgesic effect was observed with Compound 58, 30 min after oral dosing. This effect lasted for 2–3 hours. $ED_{50}$ values of 23.1 and 1.7 were obtained for Compound 58 and tramadol respectively.

The analgesic activity of the compounds was demonstrated in another in vivo test which uses mice as the test animal. The test was essentially described by N. Eddy and D. Leimbach, Synthetic Analgesics II Dithienylbutenyl- and Dithienylbutylamines, *J. Pharmacol. Exp. Ther.*, 107, 385–93 (1953) and J. O'Callaghan and S. Holtzman, Qualification of the Analgesic Activity of Narcotic Antagonists by a Modified Hot-Plate Procedure, *J. Pharmacol. Exp. Ther*, 192, 497–505 (1975), with minor modifications. Mice were placed on a heated surface (48° C.) and the time interval (seconds) between placement and a shaking, licking, or tucking of the hind paw was recorded as the predrug latency response. This procedure was repeated 30 minutes after the administration of a test compound (p.o., 10 mL/kg). The percent maximum possible antinociceptive effect (% MPE) was determined using the following formula: % MPE=100× (Test latency−Predrug latency)/(Cutoff time−Predrug Latency), using the predrug latency of each animal and cutoff time established to prevent injury to the animal. The cutoff time was 90s.

The $ED_{50}$ value and 95% confidence intervals were determined using a computer-assisted linear regression analysis of the dose-response curve, including an analysis of variance test for linearity. Oral dosing of Compound 58 produced an analgesic effect after 15 min. This effect lasted for one hour. $ED_{50}$ values of 14.2 and 28.3 were found for Compound 58 and tramadol respectively.

What is claimed is:

1. A compound of Formula I

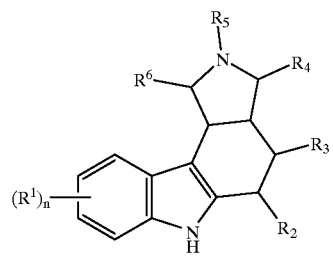

wherein:

R¹ is independently selected from one or more members of the group consisting of halogen, hydrogen, $C_{1-5}$alkyl, trifluoromethyl, $C_{1-5}$alkoxy, $C_{1-5}$alkylthio, amido, cyano, alkenyl, alkynyl, $C_{1-5}$alkoxycarbonyl, $C_{1-5}$alkylcarbonyl, phenyl, phenylcarbonyl, $C_{1-5}$alkylsulfonyl, phenylsulfonyl, substituted phenyl where the phenyl substituents are selected from group consisting of $C_{1-5}$alkyl, $C_{1-5}$alkoxy, cyano, and halogen; and substituted phenylcarbonyl where the phenyl substituents are selected from group consisting of $C_{1-5}$alkyl, $C_{1-5}$alkoxy, cyano, and halogen; and substituted phenylsulfonyl where the phenyl substituents are selected group consisting of $C_{1-5}$alkyl, $C_{1-5}$alkoxy, cyano, halogen;

R² is hydrogen, $C_{1-5}$alkyl, phenyl, phenyl$C_{1-5}$alkyl, substituted phenyl where the phenyl substituents are selected group consisting of $C_{1-5}$alkyl, $C_{1-5}$alkoxy, cyano, halogen; or substituted phenyl$C_{1-5}$alkyl where the phenyl substituents are selected group consisting of $C_{1-5}$alkyl, $C_{1-5}$alkoxy, cyano, and halogen;

R³ is hydrogen, $C_{1-5}$alkyl, phenyl, phenyl$C_{1-5}$alkyl, substituted phenyl where the phenyl substituents are selected group consisting of $C_{1-5}$alkyl, $C_{1-5}$alkoxy, cyano, halogen; or substituted phenyl$C_{1-5}$alkyl where the phenyl substituents are selected group consisting of $C_{1-5}$alkyl, $C_{1-5}$alkoxy, cyano, and halogen;

R⁴ is hydrogen or $C_{1-5}$alkyl;

R⁵ is hydrogen, $C_{1-5}$alkyl, $C_{1-5}$alkenyl, or $C_{1-5}$alkynyl

R⁶ is hydrogen or $C_{1-5}$alkyl;

n is 1–4; and pharmaceutically acceptable salts thereof.

2. The compounds of claim 1 where R², R³, R⁴, and R⁶ are hydrogen.

3. The compounds of claim 2 where R⁵ is $C_{1-5}$alkyl.

4. The compounds of claim 3 where R¹ is hydrogen, halogen, $C_{1-5}$alkyl, trifluoromethyl, or nitrile and n is 1.

5. The compounds of claim 4 where R¹ is $C_{1-5}$alkyl or hydrogen.

6. A compound of Formula I

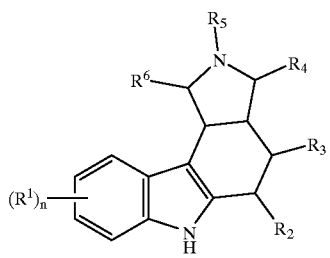

wherein: the ring junction is "cis" and
R$^1$ is independently selected from one or more members of the group consisting of halogen, hydrogen, C$_{1-5}$alkyl, trifluoromethyl, C$_{1-5}$alkoxy, C$_{1-5}$alkylthio, amido, cyano, alkenyl, alkynyl, C$_{1-5}$alkoxycarbonyl, C$_{1-5}$alkylcarbonyl, phenyl, phenylcarbonyl, C$_{1-5}$alkylsulfonyl, phenylsulfonyl, substituted phenyl
where the phenyl substituents are selected from group consisting of C$_{1-5}$alkyl, C$_{1-5}$alkoxy, cyano, and halogen; and substituted phenylcarbonyl
where the phenyl substituents are selected from group consisting of C$_{1-5}$alkyl, C$_{1-5}$alkoxy, cyano, and halogen; and substituted phenylsulfonyl
where the phenyl substituents are selected group consisting of C$_{1-5}$alkyl, C$_{1-5}$alkoxy, cyano, halogen;
R$^2$ is hydrogen, C$_{1-5}$alkyl, phenyl, phenylC$_{1-5}$alkyl, substituted phenyl
where the phenyl substituents are selected group consisting of C$_{1-5}$alkyl, C$_{1-5}$alkoxy, cyano, halogen; or substituted phenylC$_{1-5}$alkyl
where the phenyl substituents are selected group consisting of C$_{1-5}$alkyl, C$_{1-5}$alkoxy, cyano, and halogen;
R$^3$ is hydrogen, C$_{1-5}$alkyl, phenyl, phenylC$_{1-5}$alkyl, substituted phenyl
where the phenyl substituents are selected group consisting of C$_{1-5}$alkyl, C$_{1-5}$alkoxy, cyano, halogen; or substituted phenylC$_{1-5}$alkyl
where the phenyl substituents are selected group consisting of C$_{1-5}$alkyl, C$_{1-5}$alkoxy, cyano, and halogen;
R$^4$ is hydrogen or C$_{1-5}$alkyl;
R$^5$ is hydrogen, C$_{1-5}$alkyl, C$_{1-5}$alkenyl, or C$_{1-5}$alkynyl R$^6$ is hydrogen or C$_{1-5}$alkyl;
n is 1–4; and
pharmaceutically acceptable salts thereof.

7. The compounds of claim 6 where R$^5$ is C$_{1-5}$alkyl.

8. The compounds of claim 7 where R$^1$ is hydrogen, halogen, C$_{1-5}$alkyl, trifluoromethyl, or nitrile and n is 1.

9. Compounds and pharmaceutically acceptable salts thereof selected from the group consisting of (S)-(+)-3aα,10cα-4,5,6,10c-octahydro-2-methylpyrrolo[3,4-c]carbazole, (R)-(−)-3aα,10cα-4,5,6,10c-octahydro-2-methylpyrrolo[3,4-c]carbazole, (+)-3aα-10cα-4,5,6,10c-octahydro-8-fluoro-2-methylpyrrolo[3,4-c]carbazole, (−)-3aα,10cα-4,5,6,10c-octahyddro-8-fluoro-2-methylpyrrolo[3,4-c]carbazole, (+)-3aα, 10cα-4,5,6,10c-octahydro-2,7-dimethylpyrrolo[3,4-c]carbazole, (±)-3aα,10cβ-1,2,3,3a,4,5,6,10c-octahydro-2-methylpyrrolo[3,4-c]carbazole, and (±)- 3aα,10cβ-1,2,3,3a,4,5,6,10c-octahydro-10-fluoro-2-methylpyrrolo[3,4-c]carbazole.

10. A compound (R)-(−)-3aα,10cα-4,5,6,10c-octahydro-2-methylpyrrolo[3,4-c]carbazole and pharmaceutically acceptable salts thereof.

11. A pharmaceutical composition comprising a compound according to claim 1 and a pharmaceutically acceptable carrier or diluent.

12. A pharmaceutical composition comprising a compound according to claim 4 and a pharmaceutically acceptable carrier or diluent.

13. A method of alleviating pain comprising administering a compound of claim 1 to a patient at an effective dose.

14. A method of alleviating pain comprising administering a compound of claim 4 to a patient at an effective dose.

15. A method of alleviating pain comprising administering a compound of claim 8 to a patient at an effective dose.

16. The method of claim 13 where the compound is administered orally and an effective dose is 5–1000 mg/kg daily.

17. The method of claim 15 where the dose is 25–100 mg/kg daily.

18. A method of treating diseases associated with the α-adrenergic receptor comprising administering an effective dose of a compound of Formula I.

* * * * *